(12) United States Patent
Miles et al.

(10) Patent No.: US 11,064,934 B2
(45) Date of Patent: Jul. 20, 2021

(54) SURGICAL ACCESS SYSTEM AND RELATED METHODS

(71) Applicant: NuVasive, Inc., San Diego, CA (US)

(72) Inventors: Patrick Miles, San Diego, CA (US); Scot Martinelli, San Diego, CA (US); Eric Finley, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 16/443,806

(22) Filed: Jun. 17, 2019

(65) Prior Publication Data

US 2019/0328378 A1 Oct. 31, 2019

Related U.S. Application Data

(60) Continuation of application No. 15/439,889, filed on Feb. 22, 2017, now Pat. No. 10,357,233, which is a
(Continued)

(51) Int. Cl.
*A61B 17/02* (2006.01)
*A61B 1/32* (2006.01)
(Continued)

(52) U.S. Cl.
CPC ............... *A61B 5/389* (2021.01); *A61B 1/06* (2013.01); *A61B 1/32* (2013.01); *A61B 5/05* (2013.01); *A61B 5/1104* (2013.01); *A61B 5/296* (2021.01); *A61B 5/4893* (2013.01); *A61B 17/02* (2013.01); *A61B 17/025* (2013.01);
(Continued)

(58) Field of Classification Search
CPC ... A61B 5/0488; A61B 90/37; A61B 17/0206; A61B 17/025; A61B 17/0218; A61B 1/06; A61B 1/32; A61B 5/0492; A61B 5/05; A61B 5/1104; A61B 5/4893; A61B 17/02; A61B 2017/00473; A61B 2017/00039; A61B 2017/0262; A61B 2505/05; A61B 2017/0256; A61B 2560/045; A61B 5/389; A61B 5/296; A61N 1/0551; Y10S 606/909
See application file for complete search history.

(56) References Cited

U.S. PATENT DOCUMENTS 208,227 A 9/1878 Dorr
509,226 A 11/1893 Kellogg
(Continued)

FOREIGN PATENT DOCUMENTS

DE 29908259 U1 7/1999
DE 10048790 A1 4/2002
(Continued)

OTHER PUBLICATIONS

International Search report dated Apr. 27, 2001 for International Application No. PCT/US00/32329, 9 pages.
(Continued)

*Primary Examiner* — Mark W. Bockelman

(57) ABSTRACT

A surgical access system including a tissue distraction assembly and a tissue refraction assembly, both of which may be equipped with one or more electrodes for use in detecting the existence of (and optionally the distance and/or direction to) neural structures before, during, and after the establishment of an operative corridor to a surgical target site.

9 Claims, 22 Drawing Sheets

Related U.S. Application Data continuation of application No. 14/598,043, filed on Jan. 15, 2015, now Pat. No. 9,610,071, which is a continuation of application No. 14/299,800, filed on Jun. 9, 2014, now Pat. No. 8,942,801, which is a continuation of application No. 14/052,271, filed on Oct. 11, 2013, now Pat. No. 8,764,649, which is a continuation of application No. 13/742,268, filed on Jan. 15, 2013, now Pat. No. 8,556,808, which is a continuation of application No. 12/623,016, filed on Nov. 20, 2009, now Pat. No. 8,355,780, which is a division of application No. 11/789,284, filed on Apr. 23, 2007, now Pat. No. 8,016,767, which is a continuation of application No. 11/137,169, filed on May 25, 2005, now Pat. No. 7,207,949, which is a continuation of application No. PCT/US2004/031768, filed on Sep. 27, 2004.

(60) Provisional application No. 60/506,136, filed on Sep. 25, 2003.

(51) Int. Cl.

| | | |
|---|---|---|
| *A61B 5/0488* | (2006.01) | |
| *A61B 1/06* | (2006.01) | |
| *A61B 90/00* | (2016.01) | |
| *A61B 5/0492* | (2006.01) | |
| *A61B 5/05* | (2021.01) | |
| *A61B 5/11* | (2006.01) | |
| *A61B 5/00* | (2006.01) | |
| *A61N 1/05* | (2006.01) | |
| *A61B 5/389* | (2021.01) | |
| *A61B 5/296* | (2021.01) | |
| *A61B 17/00* | (2006.01) | |

(52) U.S. Cl.
CPC ...... *A61B 17/0206* (2013.01); *A61B 17/0218* (2013.01); *A61B 90/37* (2016.02); *A61N 1/0551* (2013.01); *A61B 2017/00039* (2013.01); *A61B 2017/00473* (2013.01); *A61B 2017/0256* (2013.01); *A61B 2017/0262* (2013.01); *A61B 2505/05* (2013.01); *A61B 2560/045* (2013.01); *Y10S 606/909* (2013.01)

(56) References Cited

U.S. PATENT DOCUMENTS

| | | |
|---|---|---|
| 972,983 A | 10/1910 | Arthur |
| 1,003,232 A | 9/1911 | Cerbo |
| 1,044,348 A | 11/1912 | Cerbo |
| 1,328,624 A | 1/1920 | Graham |
| 1,548,184 A | 8/1925 | Cameron |
| 1,919,120 A | 7/1933 | O'Connor et al. |
| 2,704,061 A | 3/1955 | Amspacker |
| 2,704,064 A | 3/1955 | Fizzell et al. |
| 2,736,002 A | 2/1956 | Oriel |
| 2,808,826 A | 10/1957 | Reiner et al. |
| 2,840,082 A | 6/1958 | Salvatore |
| 3,364,929 A | 1/1968 | Ide et al. |
| 3,664,329 A | 5/1972 | Naylor |
| 3,682,162 A | 8/1972 | Colyer |
| 3,740,839 A | 6/1973 | Otte et al. |
| 3,785,368 A | 1/1974 | McCarthy et al. |
| 3,803,716 A | 4/1974 | Garnier |
| 3,830,226 A | 8/1974 | Staub et al. |
| 3,957,036 A | 5/1976 | Normann |
| D245,789 S | 9/1977 | Shea |
| 4,099,519 A | 7/1978 | Warren |
| 4,164,214 A | 8/1979 | Pelzner et al. |
| 4,207,897 A | 6/1980 | Evatt et al. |
| 4,224,949 A | 9/1980 | Scott et al. |
| 4,226,228 A | 10/1980 | Shin et al. |
| 4,226,288 A | 10/1980 | Collins, Jr. |
| 4,235,242 A | 11/1980 | Heule et al. |
| 4,285,347 A | 8/1981 | Hess |
| 4,291,705 A | 9/1981 | Severinghaus et al. |
| 4,449,532 A | 5/1984 | Storz |
| 4,461,300 A | 7/1984 | Christensen |
| 4,512,351 A | 4/1985 | Pohndorf |
| 4,515,168 A | 5/1985 | Chester et al. |
| 4,519,403 A | 5/1985 | Dickhudt |
| 4,545,374 A | 10/1985 | Jacobson |
| 4,561,445 A | 12/1985 | Berke et al. |
| 4,562,832 A | 1/1986 | Wilder et al. |
| 4,573,448 A | 3/1986 | Kambin |
| 4,592,369 A | 6/1986 | Davis et al. |
| 4,595,013 A | 6/1986 | Jones et al. |
| 4,595,018 A | 6/1986 | Rantala |
| 4,611,597 A | 9/1986 | Kraus |
| 4,616,635 A | 10/1986 | Caspar et al. |
| 4,633,889 A | 1/1987 | Talalla et al. |
| 4,658,835 A | 4/1987 | Pohndorf |
| D295,445 S | 4/1988 | Freeman |
| 4,744,371 A | 5/1988 | Harris |
| 4,753,223 A | 6/1988 | Bremer |
| 4,759,377 A | 7/1988 | Dykstra |
| 4,784,150 A | 11/1988 | Voorhies et al. |
| 4,807,642 A | 2/1989 | Brown |
| D300,561 S | 4/1989 | Asa |
| 4,892,105 A | 1/1990 | Prass |
| 4,913,134 A | 4/1990 | Luque |
| 4,917,274 A | 4/1990 | Asa et al. |
| 4,917,704 A | 4/1990 | Frey et al. |
| 4,926,865 A | 5/1990 | Oman |
| 4,950,257 A | 8/1990 | Hibbs et al. |
| 4,962,766 A | 10/1990 | Herzon |
| 4,964,411 A | 10/1990 | Johnson et al. |
| 5,007,902 A | 4/1991 | Witt |
| 5,015,247 A | 5/1991 | Michelson |
| 5,045,054 A | 9/1991 | Hood et al. |
| 5,052,373 A | 10/1991 | Michelson |
| 5,058,602 A | 10/1991 | Brody |
| 5,081,990 A | 1/1992 | Deletis |
| 5,092,344 A | 3/1992 | Lee |
| 5,127,403 A | 7/1992 | Brownlee |
| 5,161,533 A | 11/1992 | Prass et al. |
| 5,171,279 A | 12/1992 | Mathews |
| 5,178,133 A | 1/1993 | Pena |
| 5,190,561 A | 3/1993 | Graber |
| 5,192,327 A | 3/1993 | Brantigan |
| 5,195,541 A | 3/1993 | Obenchain |
| 5,196,015 A | 3/1993 | Neubardt |
| 5,215,100 A | 6/1993 | Spitz et al. |
| 5,231,974 A | 8/1993 | Giglio et al. |
| RE34,390 E | 9/1993 | Culver |
| D340,521 S | 10/1993 | Heinzelman |
| 5,255,691 A | 10/1993 | Otten |
| 5,261,918 A | 11/1993 | Phillips et al. |
| 5,282,468 A | 2/1994 | Klepinski |
| 5,284,153 A | 2/1994 | Raymond et al. |
| 5,284,154 A | 2/1994 | Raymond et al. |
| 5,295,994 A | 3/1994 | Bonutti |
| 5,299,563 A | 4/1994 | Seton |
| 5,312,417 A | 5/1994 | Wilk |
| 5,313,956 A | 5/1994 | Knutsson et al. |
| 5,313,962 A | 5/1994 | Obenchain |
| 5,327,902 A | 7/1994 | Lemmen |
| 5,331,975 A | 7/1994 | Bonutti |
| 5,333,618 A | 8/1994 | Lekhtman et al. |
| 5,342,384 A | 8/1994 | Sugarbaker |
| 5,357,983 A | 10/1994 | Mathews |
| 5,375,067 A | 12/1994 | Berchin |
| 5,375,594 A | 12/1994 | Cueva |
| 5,383,876 A | 1/1995 | Nardella |
| 5,395,317 A | 3/1995 | Kambin |
| 5,425,772 A | 6/1995 | Brantigan |
| 5,433,739 A | 7/1995 | Sluijter et al. |
| 5,450,845 A | 9/1995 | Axelgaard |
| 5,458,638 A | 10/1995 | Kuslich et al. |
| 5,472,426 A | 12/1995 | Bonati et al. |

(56) References Cited

U.S. PATENT DOCUMENTS

| | | |
|---|---|---|
| 5,474,057 A | 12/1995 | Makower et al. |
| 5,474,558 A | 12/1995 | Neubardt |
| 5,480,440 A | 1/1996 | Kambin |
| 5,482,038 A | 1/1996 | Ruff |
| 5,484,437 A | 1/1996 | Michelson |
| 5,487,739 A | 1/1996 | Aebischer et al. |
| 5,509,893 A | 4/1996 | Pracas |
| 5,514,153 A | 5/1996 | Bonutti |
| 5,540,235 A | 7/1996 | Wilson |
| 5,545,222 A | 8/1996 | Bonutti |
| 5,549,656 A | 8/1996 | Reiss |
| 5,560,372 A | 10/1996 | Cory |
| 5,562,736 A | 10/1996 | Ray et al. |
| 5,566,678 A | 10/1996 | Cadwell et al. |
| 5,569,290 A | 10/1996 | McAfee |
| 5,571,149 A | 11/1996 | Liss et al. |
| 5,579,781 A | 12/1996 | Cooke |
| 5,593,429 A | 1/1997 | Ruff |
| 5,599,279 A | 2/1997 | Slotman et al. |
| 5,630,813 A | 5/1997 | Kieturakis |
| 5,653,761 A | 8/1997 | Pisharodi |
| 5,653,762 A | 8/1997 | Pisharodi |
| 5,667,508 A | 9/1997 | Errico et al. |
| 5,669,909 A | 9/1997 | Zdeblick et al. |
| 5,671,752 A | 9/1997 | Sinderby et al. |
| 5,681,265 A | 10/1997 | Maeda et al. |
| 5,707,359 A | 1/1998 | Bufalini |
| 5,711,307 A | 1/1998 | Smits |
| 5,716,415 A | 2/1998 | Steffee |
| 5,720,751 A | 2/1998 | Jackson |
| 5,728,046 A | 3/1998 | Mayer et al. |
| 5,728,159 A | 3/1998 | Stroever et al. |
| 5,741,253 A | 4/1998 | Michelson |
| 5,741,261 A | 4/1998 | Moskovitz et al. |
| 5,759,159 A | 6/1998 | Masreliez |
| 5,762,629 A | 6/1998 | Kambin |
| 5,766,252 A | 6/1998 | Henry et al. |
| 5,772,661 A | 6/1998 | Michelson |
| 5,775,331 A | 7/1998 | Raymond et al. |
| 5,776,144 A | 7/1998 | Leysieffer et al. |
| 5,779,642 A | 7/1998 | Nightengale |
| 5,785,658 A | 7/1998 | Benaron et al. |
| 5,792,044 A | 8/1998 | Foley et al. |
| 5,797,854 A | 8/1998 | Hedgecock |
| 5,797,909 A | 8/1998 | Michelson |
| 5,800,550 A | 9/1998 | Sertich |
| 5,813,978 A | 9/1998 | Jako |
| 5,814,073 A | 9/1998 | Bonutti |
| 5,814,084 A | 9/1998 | Grivas et al. |
| 5,830,151 A | 11/1998 | Hadzic et al. |
| 5,851,191 A | 12/1998 | Gozani |
| 5,851,208 A | 12/1998 | Trott |
| 5,853,373 A | 12/1998 | Griffith et al. |
| 5,860,973 A | 1/1999 | Michelson |
| 5,862,314 A | 1/1999 | Jeddeloh |
| 5,865,845 A | 2/1999 | Thalgott |
| 5,872,314 A | 2/1999 | Clinton |
| 5,885,210 A | 3/1999 | Cox |
| 5,885,219 A | 3/1999 | Nightengale |
| 5,888,196 A | 3/1999 | Bonutti |
| 5,888,224 A | 3/1999 | Beckers et al. |
| 5,891,147 A | 4/1999 | Moskovitz et al. |
| 5,893,890 A | 4/1999 | Pisharodi |
| 5,902,231 A | 5/1999 | Foley et al. |
| 5,910,315 A | 6/1999 | Stevenson et al. |
| 5,928,139 A | 7/1999 | Koros et al. |
| 5,928,158 A | 7/1999 | Aristides |
| 5,935,131 A | 8/1999 | Bonutti |
| 5,938,688 A | 8/1999 | Schiff |
| 5,944,658 A | 8/1999 | Koros et al. |
| 5,954,769 A | 9/1999 | Rosenlicht |
| 5,968,098 A | 10/1999 | Winslow |
| 5,976,094 A | 11/1999 | Gozani |
| 5,976,146 A | 11/1999 | Ogawa et al. |
| 5,993,474 A | 11/1999 | Ouchi |
| 6,004,262 A | 12/1999 | Putz et al. |
| 6,004,312 A | 12/1999 | Finneran et al. |
| 6,004,326 A | 12/1999 | Castro et al. |
| 6,007,487 A | 12/1999 | Foley et al. |
| 6,008,433 A | 12/1999 | Stone |
| 6,010,520 A | 1/2000 | Pattison |
| 6,015,436 A | 1/2000 | Schoenhoeffer |
| 6,024,696 A | 2/2000 | Hoftman et al. |
| 6,024,697 A | 2/2000 | Pisarik |
| 6,027,456 A | 2/2000 | Feler et al. |
| 6,033,405 A | 3/2000 | Winslow et al. |
| 6,036,638 A | 3/2000 | Nwawka |
| 6,038,469 A | 3/2000 | Karlsson et al. |
| 6,038,477 A | 3/2000 | Kayyali |
| 6,039,761 A | 3/2000 | Li et al. |
| 6,042,582 A | 3/2000 | Ray |
| 6,045,580 A | 4/2000 | Scarborough et al. |
| 6,048,342 A | 4/2000 | Zucherman et al. |
| 6,050,992 A | 4/2000 | Nichols |
| 6,059,829 A | 5/2000 | Schlaepfer et al. |
| 6,063,088 A | 5/2000 | Winslow |
| 6,074,343 A | 6/2000 | Nathanson et al. |
| 6,080,105 A | 6/2000 | Spears |
| 6,083,154 A | 7/2000 | Liu et al. |
| 6,083,225 A | 7/2000 | Winslow et al. |
| 6,095,987 A | 8/2000 | Shmulewitz et al. |
| 6,096,080 A | 8/2000 | Nicholson et al. |
| 6,104,957 A | 8/2000 | Alo et al. |
| 6,104,960 A | 8/2000 | Duysens et al. |
| 6,113,638 A | 9/2000 | Williams et al. |
| 6,120,503 A | 9/2000 | Michelson |
| 6,120,506 A | 9/2000 | Kohrs et al. |
| 6,126,660 A | 10/2000 | Dietz |
| 6,132,386 A | 10/2000 | Gozani et al. |
| 6,132,387 A | 10/2000 | Gozani et al. |
| 6,135,965 A | 10/2000 | Tumer et al. |
| 6,139,493 A | 10/2000 | Koros et al. |
| 6,142,931 A | 11/2000 | Kaji |
| 6,146,335 A | 11/2000 | Gozani |
| 6,152,871 A | 11/2000 | Foley et al. |
| 6,159,179 A | 12/2000 | Simonson |
| 6,159,211 A | 12/2000 | Boriani et al. |
| 6,159,215 A | 12/2000 | Urbahns et al. |
| 6,159,230 A | 12/2000 | Samuels |
| 6,161,047 A | 12/2000 | King et al. |
| 6,174,311 B1 | 1/2001 | Branch et al. |
| 6,181,961 B1 | 1/2001 | Prass |
| 6,187,000 B1 | 2/2001 | Davison et al. |
| 6,193,756 B1 | 2/2001 | Studer et al. |
| 6,200,347 B1 | 3/2001 | Anderson et al. |
| 6,206,826 B1 | 3/2001 | Mathews et al. |
| 6,206,922 B1 | 3/2001 | Zdeblick et al. |
| 6,217,509 B1 | 4/2001 | Foley et al. |
| 6,224,545 B1 | 5/2001 | Cocchia et al. |
| 6,224,549 B1 | 5/2001 | Drongelen |
| 6,224,607 B1 | 5/2001 | Michelson |
| 6,224,631 B1 | 5/2001 | Kohrs |
| 6,241,771 B1 | 6/2001 | Gresser et al. |
| 6,245,082 B1 | 6/2001 | Gellman et al. |
| 6,251,140 B1 | 6/2001 | Marino et al. |
| 6,258,125 B1 | 7/2001 | Paul et al. |
| 6,259,945 B1 | 7/2001 | Epstein et al. |
| 6,264,651 B1 | 7/2001 | Underwood et al. |
| 6,266,558 B1 | 7/2001 | Gozani et al. |
| 6,273,905 B1 | 8/2001 | Streeter |
| 6,277,149 B1 | 8/2001 | Boyle et al. |
| 6,292,701 B1 | 9/2001 | Prass et al. |
| 6,306,100 B1 | 10/2001 | Prass |
| 6,308,712 B1 | 10/2001 | Shaw |
| 6,312,392 B1 | 11/2001 | Herzon |
| 6,319,257 B1 | 11/2001 | Carignan et al. |
| 6,325,764 B1 | 12/2001 | Griffith et al. |
| 6,334,068 B1 | 12/2001 | Hacker |
| 6,348,058 B1 | 2/2002 | Melkent et al. |
| 6,360,750 B1 | 3/2002 | Gerber et al. |
| 6,371,968 B1 | 4/2002 | Kogasaka et al. |
| 6,371,989 B1 | 4/2002 | Chauvin et al. |
| 6,383,221 B1 | 5/2002 | Scarborough et al. |
| 6,395,007 B1 | 5/2002 | Bhatnagar et al. |

(56) References Cited

U.S. PATENT DOCUMENTS

| | | |
|---|---|---|
| 6,409,766 B1 | 6/2002 | Brett |
| 6,416,465 B2 | 7/2002 | Brau |
| 6,425,859 B1 | 7/2002 | Foley et al. |
| 6,425,887 B1 | 7/2002 | McGuckin et al. |
| 6,425,901 B1 | 7/2002 | Zhu et al. |
| 6,432,048 B1 | 8/2002 | Francois |
| 6,432,140 B1 | 8/2002 | Lin |
| 6,440,142 B1 | 8/2002 | Ralph et al. |
| 6,442,814 B1 | 9/2002 | Landry et al. |
| 6,450,952 B1 | 9/2002 | Rioux et al. |
| 6,451,015 B1 | 9/2002 | Rittman, III et al. |
| 6,454,806 B1 | 9/2002 | Cohen et al. |
| 6,466,817 B1 | 10/2002 | Kaula et al. |
| 6,468,205 B1 | 10/2002 | Mollenauer et al. |
| 6,468,207 B1 | 10/2002 | Fowler, Jr. |
| 6,468,311 B2 | 10/2002 | Boyd et al. |
| 6,491,724 B1 | 12/2002 | Ferree |
| 6,500,116 B1 | 12/2002 | Knapp |
| 6,500,128 B2 | 12/2002 | Marino |
| 6,520,907 B1 | 2/2003 | Foley et al. |
| 6,524,320 B2 | 2/2003 | Dipoto |
| 6,535,759 B1 | 3/2003 | Epstein et al. |
| D472,634 S | 4/2003 | Anderson |
| D472,650 S | 4/2003 | Green |
| 6,564,078 B1 | 5/2003 | Marino et al. |
| 6,579,244 B2 | 6/2003 | Goodwin |
| 6,595,998 B2 | 7/2003 | Johnson et al. |
| 6,599,294 B2 | 7/2003 | Fuss et al. |
| 6,620,157 B1 | 9/2003 | Dabney et al. |
| 6,626,905 B1 | 9/2003 | Schmiel et al. |
| 6,635,086 B2 | 10/2003 | Lin |
| 6,645,194 B2 | 11/2003 | Briscoe et al. |
| 6,648,895 B2 | 11/2003 | Burkus et al. |
| 6,672,019 B1 | 1/2004 | Wenz et al. |
| 6,676,703 B2 | 1/2004 | Biscup |
| 6,679,833 B2 | 1/2004 | Smith et al. |
| 6,706,067 B2 | 3/2004 | Shimp et al. |
| 6,719,692 B2 | 4/2004 | Kleffner |
| 6,746,484 B1 | 6/2004 | Liu et al. |
| 6,755,841 B2 | 6/2004 | Fraser et al. |
| 6,760,616 B2 | 7/2004 | Hoey et al. |
| 6,761,739 B2 | 7/2004 | Shepard |
| 6,770,074 B2 | 8/2004 | Michelson |
| 6,796,985 B2 | 9/2004 | Bolger et al. |
| 6,810,281 B2 | 10/2004 | Brock et al. |
| 6,819,956 B2 | 11/2004 | DiLorenzo |
| 6,824,564 B2 | 11/2004 | Crozet |
| 6,829,508 B2 | 12/2004 | Schulman et al. |
| 6,830,570 B1 | 12/2004 | Frey et al. |
| 6,847,849 B2 | 1/2005 | Mamo et al. |
| 6,849,047 B2 | 2/2005 | Goodwin |
| 6,855,105 B2 | 2/2005 | Jackson et al. |
| 6,869,398 B2 | 3/2005 | Obenchain et al. |
| 6,871,099 B1 | 3/2005 | Whitehurst et al. |
| D503,801 S | 4/2005 | Jackson |
| 6,902,569 B2 | 6/2005 | Parmer et al. |
| 6,916,330 B2 | 7/2005 | Simonson |
| 6,926,728 B2 | 8/2005 | Zucherman et al. |
| 6,929,606 B2 | 8/2005 | Ritland |
| 6,942,698 B1 | 9/2005 | Jackson |
| 6,951,538 B2 | 10/2005 | Ritland |
| 6,964,687 B1 | 11/2005 | Bernard et al. |
| 6,979,353 B2 | 12/2005 | Bresina |
| 6,984,245 B2 | 1/2006 | McGahan et al. |
| 6,986,788 B2 | 1/2006 | Paul et al. |
| 6,989,031 B2 | 1/2006 | Michelson |
| 7,018,416 B2 | 3/2006 | Hanson et al. |
| 7,047,082 B1 | 5/2006 | Schrom et al. |
| 7,050,848 B2 | 5/2006 | Hoey et al. |
| 7,079,883 B2 | 7/2006 | Marino et al. |
| 7,089,059 B1 | 8/2006 | Pless |
| D530,423 S | 10/2006 | Miles et al. |
| 7,166,113 B2 | 1/2007 | Arambula et al. |
| 7,177,677 B2 | 2/2007 | Kaula et al. |
| 7,198,598 B2 | 4/2007 | Smith et al. |
| 7,226,451 B2 | 6/2007 | Shluzas et al. |
| 7,261,688 B2 | 8/2007 | Smith et al. |
| 7,470,236 B1 | 12/2008 | Kelleher et al. |
| 7,473,222 B2 | 1/2009 | Dewey et al. |
| 7,481,766 B2 | 1/2009 | Lee et al. |
| 7,522,953 B2 | 4/2009 | Gharib et al. |
| 7,556,601 B2 | 7/2009 | Branch et al. |
| 7,582,058 B1 | 9/2009 | Miles et al. |
| 7,643,884 B2 | 1/2010 | Pond et al. |
| 7,691,057 B2 | 4/2010 | Miles et al. |
| 7,693,562 B2 | 4/2010 | Marino et al. |
| 7,717,959 B2 | 5/2010 | William et al. |
| 7,819,801 B2 | 10/2010 | Miles et al. |
| 7,892,173 B2 | 2/2011 | Miles et al. |
| 7,905,840 B2 | 3/2011 | Pimenta et al. |
| 7,918,891 B1 | 4/2011 | Curran et al. |
| 7,920,922 B2 | 4/2011 | Kaula et al. |
| 7,935,051 B2 | 5/2011 | Miles et al. |
| 7,962,191 B2 | 6/2011 | Marino et al. |
| 7,963,927 B2 | 6/2011 | Kelleher et al. |
| 7,991,463 B2 | 8/2011 | Kelleher et al. |
| 8,000,782 B2 | 8/2011 | Gharib et al. |
| 8,005,535 B2 | 8/2011 | Gharib et al. |
| 8,021,430 B2 | 9/2011 | Michelson |
| 8,055,349 B2 | 11/2011 | Kaula et al. |
| 8,068,912 B2 | 11/2011 | Gharib et al. |
| 8,114,019 B2 | 2/2012 | Miles et al. |
| 8,133,173 B2 | 3/2012 | Miles et al. |
| 8,137,284 B2 | 3/2012 | Miles et al. |
| 8,172,750 B2 | 5/2012 | Miles et al. |
| 8,182,423 B2 | 5/2012 | Miles et al. |
| 8,187,179 B2 | 5/2012 | Miles et al. |
| 8,187,334 B2 | 5/2012 | Curran et al. |
| 8,192,356 B2 | 6/2012 | Miles et al. |
| 8,192,357 B2 | 6/2012 | Miles et al. |
| 8,244,343 B2 | 8/2012 | Gharib et al. |
| 8,246,686 B1 | 8/2012 | Curran et al. |
| 8,251,997 B2 | 8/2012 | Michelson |
| 8,303,458 B2 | 11/2012 | Fukano et al. |
| 8,303,498 B2 | 11/2012 | Miles et al. |
| 8,303,515 B2 | 11/2012 | Pimenta et al. |
| 8,337,410 B2 | 12/2012 | Kelleher et al. |
| 8,343,046 B2 | 1/2013 | Miles et al. |
| 8,343,224 B2 | 1/2013 | Lynn et al. |
| 8,361,156 B2 | 1/2013 | Curran et al. |
| 8,388,527 B2 | 3/2013 | Miles et al. |
| 8,403,841 B2 | 3/2013 | Miles et al. |
| 8,439,832 B2 | 5/2013 | Miles et al. |
| 8,489,170 B2 | 7/2013 | Marino et al. |
| 8,500,634 B2 | 8/2013 | Miles et al. |
| 8,512,235 B2 | 8/2013 | Miles et al. |
| 8,523,768 B2 | 9/2013 | Miles et al. |
| 8,548,579 B2 | 10/2013 | Gharib et al. |
| 8,550,994 B2 | 10/2013 | Miles et al. |
| 8,562,521 B2 | 10/2013 | Miles et al. |
| 8,574,301 B2 | 11/2013 | Curran et al. |
| 8,591,432 B2 | 11/2013 | Pimenta et al. |
| 8,602,982 B2 | 12/2013 | Miles et al. |
| 8,608,804 B2 | 12/2013 | Curran et al. |
| 8,628,469 B2 | 1/2014 | Miles et al. |
| 8,634,904 B2 | 1/2014 | Kaula et al. |
| 8,663,100 B2 | 3/2014 | Miles et al. |
| 8,672,840 B2 | 3/2014 | Miles et al. |
| 8,673,005 B1 | 3/2014 | Pimenta et al. |
| 8,679,006 B2 | 3/2014 | Miles et al. |
| 8,685,105 B2 | 4/2014 | Curran et al. |
| 8,696,559 B2 | 4/2014 | Miles et al. |
| 8,708,899 B2 | 4/2014 | Miles et al. |
| 8,738,123 B2 | 5/2014 | Gharib et al. |
| 8,740,783 B2 | 6/2014 | Gharib et al. |
| 8,747,307 B2 | 6/2014 | Miles et al. |
| 8,753,270 B2 | 6/2014 | Miles et al. |
| 8,753,271 B1 | 6/2014 | Miles et al. |
| 8,768,450 B2 | 7/2014 | Gharib et al. |
| 8,780,899 B2 | 7/2014 | Tillman et al. |
| 8,812,116 B2 | 8/2014 | Kaula et al. |
| 8,814,940 B2 | 8/2014 | Curran et al. |
| 8,821,396 B1 | 9/2014 | Miles et al. |
| 8,915,846 B2 | 12/2014 | Miles et al. |

(56) References Cited

U.S. PATENT DOCUMENTS

| | | |
|---|---|---|
| 8,945,004 B2 | 2/2015 | Miles et al. |
| 8,956,283 B2 | 2/2015 | Miles et al. |
| 8,958,869 B2 | 2/2015 | Kelleher et al. |
| 8,977,352 B2 | 3/2015 | Gharib et al. |
| 9,014,776 B2 | 4/2015 | Marino et al. |
| 9,037,250 B2 | 5/2015 | Kaula et al. |
| 9,180,021 B2 | 11/2015 | Curran et al. |
| 9,186,261 B2 | 11/2015 | Pimenta et al. |
| 9,204,871 B2 | 12/2015 | Miles et al. |
| 9,265,493 B2 | 2/2016 | Miles et al. |
| 9,301,743 B2 | 4/2016 | Miles et al. |
| 9,314,152 B2 | 4/2016 | Pimenta et al. |
| 9,387,090 B2 | 7/2016 | Arnold et al. |
| 9,456,783 B2 | 10/2016 | Kaula et al. |
| 9,468,405 B2 | 10/2016 | Miles et al. |
| 9,474,627 B2 | 10/2016 | Curran et al. |
| 9,486,329 B2 | 11/2016 | Pimenta et al. |
| 9,572,562 B2 | 2/2017 | Miles et al. |
| 9,610,071 B2 | 4/2017 | Miles et al. |
| 9,636,233 B2 | 5/2017 | Arnold et al. |
| 10,357,233 B2 * | 7/2019 | Miles .................. A61B 5/05 |
| 2001/0037123 A1 | 11/2001 | Hancock |
| 2001/0039949 A1 | 11/2001 | Loubser |
| 2001/0056280 A1 | 12/2001 | Underwood et al. |
| 2002/0007129 A1 | 1/2002 | Marino |
| 2002/0010392 A1 | 1/2002 | Desai |
| 2002/0016592 A1 | 2/2002 | Branch et al. |
| 2002/0065481 A1 | 5/2002 | Cory et al. |
| 2002/0072686 A1 | 6/2002 | Hoey et al. |
| 2002/0077632 A1 | 6/2002 | Tsou |
| 2002/0123744 A1 | 9/2002 | Reynard |
| 2002/0123780 A1 | 9/2002 | Grill et al. |
| 2002/0147387 A1 | 10/2002 | Paolitto et al. |
| 2002/0161415 A1 | 10/2002 | Cohen et al. |
| 2002/0193843 A1 | 12/2002 | Hill et al. |
| 2003/0032966 A1 | 2/2003 | Foley et al. |
| 2003/0070682 A1 | 4/2003 | Wilson et al. |
| 2003/0083688 A1 | 5/2003 | Simonson |
| 2003/0105503 A1 | 6/2003 | Marino |
| 2003/0105528 A1 | 6/2003 | Shimp et al. |
| 2003/0109928 A1 | 6/2003 | Pasquet et al. |
| 2003/0139648 A1 | 7/2003 | Foley et al. |
| 2003/0149341 A1 | 8/2003 | Clifton |
| 2003/0225405 A1 | 12/2003 | Weiner |
| 2003/0236544 A1 | 12/2003 | Lunsford et al. |
| 2004/0181165 A1 | 9/2004 | Hoey et al. |
| 2004/0199084 A1 | 10/2004 | Kelleher et al. |
| 2004/0225228 A1 | 11/2004 | Ferree |
| 2004/0230191 A1 | 11/2004 | Frey et al. |
| 2005/0004593 A1 | 1/2005 | Simonson |
| 2005/0004623 A1 | 1/2005 | Miles et al. |
| 2005/0033380 A1 | 2/2005 | Tanner et al. |
| 2005/0060006 A1 | 3/2005 | Pflueger et al. |
| 2005/0075578 A1 | 4/2005 | Gharib et al. |
| 2005/0149035 A1 | 7/2005 | Pimenta et al. |
| 2005/0149054 A1 | 7/2005 | Gorek |
| 2005/0182454 A1 | 8/2005 | Gharib et al. |
| 2005/0192575 A1 | 9/2005 | Pacheco |
| 2005/0203538 A1 | 9/2005 | Lo et al. |
| 2005/0228232 A1 | 10/2005 | Gillinov et al. |
| 2005/0277812 A1 | 12/2005 | Myles |
| 2006/0025703 A1 | 2/2006 | Miles et al. |
| 2006/0052826 A1 | 3/2006 | Kim et al. |
| 2006/0052828 A1 | 3/2006 | Kim et al. |
| 2006/0069315 A1 | 3/2006 | Miles et al. |
| 2006/0224078 A1 | 10/2006 | Hoey et al. |
| 2006/0235529 A1 | 10/2006 | Ralph et al. |
| 2006/0247658 A1 | 11/2006 | Pond et al. |
| 2007/0016097 A1 | 1/2007 | Farquhar et al. |
| 2007/0049931 A1 | 3/2007 | Justis et al. |
| 2007/0049962 A1 | 3/2007 | Marino et al. |
| 2007/0072475 A1 | 3/2007 | Justin et al. |
| 2007/0100212 A1 | 5/2007 | Pimenta et al. |
| 2007/0198062 A1 | 8/2007 | Miles et al. |
| 2007/0208228 A1 | 9/2007 | Pavento et al. |
| 2007/0260317 A1 | 11/2007 | Ankney et al. |
| 2007/0270842 A1 | 11/2007 | Bankoski et al. |
| 2007/0293782 A1 | 12/2007 | Marino |
| 2008/0058606 A1 | 3/2008 | Miles et al. |
| 2008/0058838 A1 | 3/2008 | Steinberg |
| 2008/0064976 A1 | 3/2008 | Kelleher et al. |
| 2008/0064977 A1 | 3/2008 | Kelleher et al. |
| 2008/0065135 A1 | 3/2008 | Marino et al. |
| 2008/0065144 A1 | 3/2008 | Marino et al. |
| 2008/0065178 A1 | 3/2008 | Kelleher et al. |
| 2008/0071191 A1 | 3/2008 | Kelleher et al. |
| 2008/0077138 A1 | 3/2008 | Cohen et al. |
| 2008/0097164 A1 | 4/2008 | Miles et al. |
| 2008/0103601 A1 | 5/2008 | Biro et al. |
| 2008/0146885 A1 | 6/2008 | Protopsaltis |
| 2008/0183214 A1 | 7/2008 | Copp et al. |
| 2008/0221394 A1 | 9/2008 | Melkent et al. |
| 2008/0288077 A1 | 11/2008 | Reo et al. |
| 2008/0300465 A1 | 12/2008 | Feigenwinter et al. |
| 2009/0030519 A1 | 1/2009 | Falahee |
| 2009/0124860 A1 | 5/2009 | Miles et al. |
| 2009/0132049 A1 | 5/2009 | Carver et al. |
| 2009/0138050 A1 | 5/2009 | Ferree |
| 2009/0138090 A1 | 5/2009 | Hurlbert et al. |
| 2009/0192403 A1 | 7/2009 | Gharib et al. |
| 2009/0204016 A1 | 8/2009 | Gharib et al. |
| 2010/0069783 A1 | 3/2010 | Miles et al. |
| 2010/0106251 A1 | 4/2010 | Kast |
| 2010/0130827 A1 | 5/2010 | Pimenta et al. |
| 2010/0152603 A1 | 6/2010 | Miles et al. |
| 2010/0160738 A1 | 6/2010 | Miles et al. |
| 2010/0174146 A1 | 7/2010 | Miles et al. |
| 2010/0174148 A1 | 7/2010 | Miles et al. |
| 2010/0228350 A1 | 9/2010 | Gornet et al. |
| 2011/0046448 A1 | 2/2011 | Paolitto et al. |
| 2011/0218631 A1 | 9/2011 | Woodburn, Sr. et al. |
| 2011/0313530 A1 | 12/2011 | Gharib et al. |
| 2012/0238822 A1 | 9/2012 | Miles et al. |
| 2012/0238893 A1 | 9/2012 | Farquhar et al. |
| 2013/0331943 A1 | 12/2013 | Arnold et al. |
| 2014/0235950 A1 | 8/2014 | Miles et al. |
| 2014/0288374 A1 | 9/2014 | Miles et al. |
| 2014/0288375 A1 | 9/2014 | Miles et al. |
| 2015/0150693 A1 | 6/2015 | Gharib et al. |
| 2015/0157227 A1 | 6/2015 | Kelleher et al. |
| 2015/0157228 A1 | 6/2015 | Marino et al. |
| 2015/0282948 A1 | 10/2015 | Arnold et al. |
| 2016/0120530 A1 | 5/2016 | Miles et al. |
| 2016/0174958 A1 | 6/2016 | Miles et al. |
| 2016/0174959 A1 | 6/2016 | Miles et al. |
| 2016/0192921 A1 | 7/2016 | Pimenta et al. |
| 2016/0374613 A1 | 12/2016 | Kaula et al. |
| 2017/0007421 A1 | 1/2017 | Curran et al. |
| 2017/0020503 A1 | 1/2017 | Miles et al. |
| 2017/0027712 A1 | 2/2017 | Pimenta et al. |
| 2017/0143514 A1 | 5/2017 | Gharib et al. |
| 2017/0143515 A1 | 5/2017 | Gharib et al. |
| 2017/0164938 A1 | 6/2017 | Miles et al. |
| 2017/0172558 A1 | 6/2017 | Miles et al. |

FOREIGN PATENT DOCUMENTS

| | | |
|---|---|---|
| EP | 0334116 A1 | 9/1989 |
| EP | 0567424 A1 | 10/1993 |
| EP | 0972538 A2 | 1/2000 |
| EP | 1002500 A1 | 5/2000 |
| FR | 2795624 A1 | 1/2001 |
| JP | 793186 | 5/1990 |
| JP | 10-014928 | 3/1996 |
| KR | 3019990007098 | 11/1999 |
| WO | WO-9428824 A2 | 12/1994 |
| WO | WO-9700702 A1 | 1/1997 |
| WO | WO-9823324 A1 | 6/1998 |
| WO | WO-9952446 A2 | 10/1999 |
| WO | WO-0027291 A1 | 5/2000 |
| WO | WO-0038574 A1 | 7/2000 |
| WO | WO-0044288 A1 | 8/2000 |
| WO | WO-0062660 A1 | 10/2000 |
| WO | WO-0066217 A1 | 11/2000 |

(56) References Cited

FOREIGN PATENT DOCUMENTS

| WO | WO-0067645 A1 | 11/2000 |
| --- | --- | --- |
| WO | WO-0108563 A2 | 2/2001 |
| WO | WO-0137728 A1 | 5/2001 |
| WO | WO-0160263 A1 | 8/2001 |
| WO | WO-02054960 A2 | 7/2002 |
| WO | WO-02058780 A1 | 8/2002 |
| WO | WO-02071953 A2 | 9/2002 |
| WO | WO-02087678 A1 | 11/2002 |
| WO | WO-03005887 A2 | 1/2003 |
| WO | WO-03026482 A2 | 4/2003 |
| WO | WO-03037170 A2 | 5/2003 |
| WO | WO-03084398 A1 | 10/2003 |
| WO | WO-2004064634 A1 | 8/2004 |
| WO | WO-2005013805 A2 | 2/2005 |
| WO | WO-2005030318 A1 | 4/2005 |
| WO | WO-2006042241 A2 | 4/2006 |
| WO | WO-2006066217 A2 | 6/2006 |
| WO | WO-2007035925 A2 | 3/2007 |
| WO | WO-2007136784 A2 | 11/2007 |
| WO | WO-2009055034 A1 | 4/2009 |
| WO | WO-2011059491 A1 | 5/2011 |
| WO | WO-2011059498 A1 | 5/2011 |
| WO | WO-2012026981 A1 | 3/2012 |
| WO | WO-2012103254 A2 | 8/2012 |
| WO | WO-2013028571 A1 | 2/2013 |

OTHER PUBLICATIONS

51O(K) No. K002677, approved by the FDA on Nov. 13, 2000, 634 pages.
51O(K) No. K013215, approved by the FDA on Oct. 16, 2001, 376 pages.
Acland's Video Atlas of Human Anatomy, Section 3.1.7: Paravertebral Muscles. Available online: http://aclandanatomy.com/abstract/4010463. Accessed Jul. 11, 2012.
Amended Complaint for *NuVasive, Inc.* v. *Globus Medical, Inc.*, Case No. 1:10-cv-0849 (D. Del., Oct. 5, 2010), 28 pages.
Amendment in reply to Action dated Feb. 7, 2011 and Notice dated May 12, 2011, in U.S. Appl. No. 11/789,284, dated May 17, 2011, 16 pages.
Amendment in reply dated Feb. 15, 2012 Office Action in U.S. Appl. No. 12/635,418, dated Mar. 16, 2012, 24 pages.
Anatomy of the Lumbar Spine in MED TM MicroEndoscopic Discectomy (1997 Ludann Grand Rapids MI), 14 pgs.
Anderson et al., "Pedicle screws with high electrical resistance: a potential source of error with stimulus-evoked EMG," Spine, Department of Orthopaedic Surgery University of Virginia, Jul. 15, 2002, 27(14): 1577-1581.
Axon 501(k) Notification: Epoch 2000 Neurological Workstation, Dec. 3, 1997, 464 pages.
Baulot, et al., Adjuvant Anterior Spinal Fusion Via Thoracoscopy, Lyon Chirurgical, 1994, 90(5):347-351 including English Translation and Certificate of Translation.
Bergey et al., "Endoscopic Lateral Transpsoas Approach to the Lumbar Spine," Spine, 2004, 29(15): 1681-1688.
Bose et al., Neurophysiologic Monitoring of Spinal Nerve Root Function During Instrumented Posterior Lumbar Spine Surgery, Spine, 2002,27(13):1444-1450.
"Brackmann II EMG System," Medical Electronics, 1999, 4 pages.
Brau, "Chapter 22: Anterior Retroperitoneal Muscle-Sparing approach to L2-S1 of the Lumbar Spine," Surgical Approaches to the Spine. Robert G. Watkins, MD. (ed) 2003. pp. 165-181.
Calancie, et al., Stimulus-evoked EMG monitoring during transpedicular lumboscaral spine instrumentation, Spine, 19(24), 1994, p. 2780-2786.
Clements et al., "Evoked and Spontaneous Electromyography to Evaluate Lumbosacral Pedicle Screw Placement," Spine, 1996, 21(5): 600-604.
Co-pending U.S. Appl. No. 15/498,296, filed Apr. 26, 2017.
Co-pending U.S. Appl. No. 90/013,464, filed Mar. 6, 2015.
Co-pending U.S. Appl. No. 90/013,546, filed Jul. 8, 2015.
Co-pending U.S. Appl. No. 90/013,605, filed Oct. 8, 2015.
Co-pending U.S. Appl. No. 95/001,247, filed Oct. 27, 2009.
Co-pending U.S. Appl. No. 95/001,888, filed Feb. 9, 2012.
Co-pending U.S. Appl. No. 95/001,890, filed Feb. 9, 2012.
Counterclaim Defendants' Corrected Amended Invalidity Contentions re U.S. Pat. Nos. 8,000,782; 8,005,535; 8,016,767; 8,192,356; 8,187,334; 8,361,156, D652,922; D666,294 re Case No. 3:12-cv-02738-CAB(MDD), dated Aug. 19, 2013, 30 pages.
Crock, H.V. MD., Anterior Lumbar Interbody Fusion, Clinical Orthopaedics and Related Research, Number One Hundred Sixty Five, 1982, pp. 157-163, 13 pages 454.
Danesh-Clough et al. ,"The Use of Evoked EMG in Detecting Misplaced Thoracolumbar Pedicle Screws," Spine, Orthopaedic Department Dunedin Hospital, Jun. 15, 2001, 26(12): 1313-1316.
Darden et al., "A Comparison of Impedance and Electromyogram Measurements in Detecting the Presence of Pedicle Wall Breakthrough," Spine, Charlotte Spine Center North Carolina, Jan. 15, 1998, 23(2): 256-262.
De Peretti, et al., New possibilities in L2-L5 lumbar arthrodesis using a lateral retroperitoneal approach assisted by laparoscopy: preliminary results, Eur Spine J 1996, 5: 210-216.
Decision on Appeal in Inter Partes Reexamination Control No. 95/001,247, dated Mar. 18, 2013, 49 pages.
Declaration of Daniel Schwartz, from IPR2014-00073, Oct. 12, 2013, 1226 pages.
Declaration of Daniel Schwartz, from IPR2014-00074, Oct. 12, 2013, 565 pages.
Declaration of Daniel Schwartz, from IPR2014-00075, Oct. 12, 2013, 1107 pages.
Declaration of Daniel Schwartz, from IPR2014-00076, Oct. 12, 2013, 1247 pages.
Declaration of Daniel Schwartz, from IPR2014-0081, Oct. 21, 2013, 585 pages.
Declaration of Daniel Schwartz from IPR2014-0087, Oct. 21, 2013, 585 pages.
Declaration of Daniel Schwartz, Ph.D. from IPR2014-00034, Oct. 7, 2013, 1056 pages.
Declaration of Daniel Schwartz, Ph.D. from IPR2014-00035, Oct. 7, 2013, 661 pages.
Declaration of David Hacker from IPR2014-00034, Oct. 4, 2013, 64 pages.
Declaration of David Hacker, from IPR2014-00073, Oct. 10, 2013, 64 pages.
Declaration of David Hacker, from IPR2014-00074, Oct. 10, 2013, 64 pages.
Declaration of David Hacker, from IPR2014-00075, Oct. 10, 2013, 64 pages.
Declaration of David Hacker, from IPR2014-00076, Oct. 10, 2013, 64 pages.
Declaration of David Hacker from IPR2014-00081, Oct. 10, 2013, 64 pages.
Declaration of David Hacker from IPR2014-00087, Oct. 10, 2013, 64 pages.
Declaration of Lee Grant, from IPR2014-00034, Oct. 7, 2013, 36 pages.
Declaration of Lee Grant, from IPR2014-00073, Oct. 9, 2013, 36 pages Declaration of David Hacker, from IPR2014-00073, Oct. 10, 2013, 64 pages.
Declaration of Lee Grant, from IPR2014-00074, Oct. 9, 2013, 36 pages.
Declaration of Lee Grant, from IPR2014-00076, Oct. 9, 2013, 36 pages.
Declaration of Lee Grant, from IPR2014-0081, Oct. 9, 2013, 36 pages.
Declaration of Lee Grant, from IPR2014-0087, Oct. 9, 2013, 36 pages.
Declaration of Robert G. Watkins, from IPR2014-00073, Oct. 18, 2013, 1101 pages.
Declaration of Robert G. Watkins, from IPR2014-00074, Oct. 18, 2013, 548 pages.
Declaration of Robert G. Watkins, from IPR2014-00075, Oct. 18, 2013, 674 pages.

(56) References Cited

OTHER PUBLICATIONS

Declaration of Robert G. Watkins, from IPR2014-00076, Oct. 18, 2013, 543 pages.
Defendant's Disclosure of Asserted Claims and Preliminary Infringement Contentions Regarding USP 7207949; 7470236 and 7582058, Aug. 31, 2009,21 pages.
Dezawa et al., "Retroperitoneal Laparoscopic Lateral Approach to the Lumbar Spine: A New Approach, Technique, and Clinical Trial," Journal of Spinal Disorders, 2000, 13(2): 138-143.
Dirksmeier et al., "Microendoscopic and Open Laminotomy and Discectomy in Lumbar Disc Disease" Seminars in Soine Surgery. 1999, 11(2): 138-146.
Ebraheim et al., "Anatomic Relations Between the Lumbar Pedicle and the Adjacent Neural Structures," Spine, Department of Orthopaedic Surgery Medical College of Ohio, Oct. 15, 1997, 22(20): 2338-2341.
European Search Report dated Apr. 7, 2015 for EP Application No. 12826211.0.
European Search Report dated Aug. 2, 2012 for EP Application No. 12001129.1.
European Search Report dated Sep. 28, 2009 for EP Application No. 02778359.6.
Final Written Decision from IPR 2014-00034, dated Apr. 3, 2015, 48 pages.Individual documents of the referenced court case are not being submitted herewith, as Applicant understands the documents to be readily accessible by the Examiner. However, Applicant can provide any of the documents upon request.
Final Written Decision from IPR 2014-00073, dated Apr. 3, 2015, 36 pages. Individual documents of the referenced court case are not being submitted herewith, as Applicant understands the documents to be readily accessible by the Examiner. However, Applicant can provide any of the documents upon request.
Final Written Decision from IPR 2014-00074, dated Apr. 3, 2015, 31 pages. Individual documents of the referenced court case are not being submitted herewith, as Applicant understands the documents to be readily accessible by the Examiner. However, Applicant can provide any of the documents upon request.
Final Written Decision from IPR 2014-00075, dated Apr. 3, 2015, 39 pages. Individual documents of the referenced court case are not being submitted herewith, as Applicant understands the documents to be readily accessible by the Examiner. However, Applicant can provide any of the documents upon request.
Final Written Decision from IPR 2014-00081, dated Apr. 3, 2015, 44 pages. Individual documents of the referenced court case are not being submitted herewith, as Applicant understands the documents to be readily accessible by the Examiner. However, Applicant can provide any of the documents upon request.
Final Written Decision from IPR 2014-00087, dated Apr. 3, 2015, 36 pages. Individual documents of the referenced court case are not being submitted herewith, as Applicant understands the documents to be readily accessible by the Examiner. However, Applicant can provide any of the documents upon request.
Foley and Smith, "Microendoscopic Discectomy," Techniques in Neurosurgery, 1997, 3(4):301-307.
Ford et al. "Electrical Characteristics of Peripheral Nerve Stimulators Implications for Nerve Localization," Regional Anesthesia 1984, 9: 73-77.
Friedman, Percutaneous discectomy: An alternative to chemonucleolysis, Neurosurgery, 1983, 13(5): 542-547.
Gardocki, "Tubular diskectomy minimizes collateral damage: A logical progression moves spine surgery forward," AAOS Now, 2009, 5 pages.
Glassman et al., "A Prospective Analysis of Intraoperative Electromyographic Monitoring of Pedicle Screw Placement With Computed Tomographic Scan Confirmation," Spine, 1995, 20(12): 1375-1379.
Greenblatt et al., "Needle Nerve Stimulator-Locator: Nerve Blocks with a New Instrument for Locating Nerves," Anesthesia& Analgesia 1962, 41 (5): 599-602.

Haig et al., "The Relation Among Spinal Geometry on MRI, Paraspinal Electromyographic Abnormalities, and Age in Persons Referred for Electrodiagnostic Testing of Low Back Symptoms," Spine, Department of Physical Medicine and Rehabilitation University of Michigan, Sep. 1, 2002, 27(17): 1918-1925.
Haig, "Point of view," Spine, 2002, 27(24): 2819.
Holland et al., "Higher Electrical Stimulus Intensities are Required to Activate Chronically Compressed Nerve Roots: Implications for Intraoperative Electromyographic Pedicle Screw Testing," Spine, Department of Neurology, Johns Hopkins University School of Medicine, Jan. 15, 1998, 23(2): 224-227.
Holland, "Intraoperative Electromyography During Thoracolumbar Spinal Surgery," Spine, 1998, 23(17): 1915-1922.
Hovorka et al., "Five years' experience of retroperitoneal lumbar and thoracolumbar surgery," Eur Snine J. 2000, 9(1 ): S30-S34.
In re: Nuvasive, Inc. in 2015-1670 decided on Dec. 7, 2016, 13 Pages.
In re: Nuvasive, Inc., in 2015-1672, 2015-1673 decided on Nov. 9, 2016, 16 Pages.
In re: Nuvasive, Inc. in 2015-1838 signed on May 10, 2017, 2 Pages.
In re: Nuvasive, Inc. in 2015-1839, 2015-1840 signed on May 10, 2017, 2 Pages.
In re: Nuvasive, Inc. in 2015-1841 decided on May 31, 2017, 16 Pages.
In re: Nuvasive, Inc. in 2015-1842, 2015-1843 signed on May 10, 2017, 2 Pages.
In re: Warsaw Orthopedic, Inc. in 15-1050 filed Oct. 14, 2014.
In re: Warsaw Orthopedic, Inc. in 15-1058 filed Oct. 17, 2014.
International Search Report dated Jan. 15, 2002 for International Application No. PCT/US01/18579, 6 pages.
International Search Report dated Jan. 12, 2011 for International Application No. PCT/US2010/002960.
International Search Report dated 0210912005 for International Application PCT/US2004/031768.
International Search Report dated Mar. 27, 2003 for International Application PCT/US2002/02224 7.
International Search Report dated Jun. 5, 2003 for International Application No. PCT/US2002/030617.
International Search Report dated Jul. 24, 2012 for International Application No. PCT/US2012/022600.
International Search Report dated Aug. 11, 2003 for International Application No. PCT/US02/35047, 5 pages.
International Search Report dated Aug. 12, 2003 for International Application No. PCT/US03/02056, 5 pages.
International Search Report dated Oct. 18, 2001 for International Application No. PCT/US01/18606, 6 pages.
International Search Report dated Oct. 29, 2012 for International Application No. PCT/US2012/051480.
International Search Report dated Dec. 13, 2011 for International Application No. PCT/US2011/001489.
International Search Report dated Dec. 24, 2008 for International Application No. PCT/US2008/012121.
International Search Report dated Mar. 23, 2011 for International Application No. PCT/US2010/002951.
Isley et al., "Recent Advances in Intraoperative Neuromonitoring of Spinal Cord Function: Pedicle Screw Stimulation Techniques," American Journal of Electroneurodiagnostic Technology, Jun. 1997, 37(2): 93-126.
Japanese Patent Office JP Patent Application No. 2006-528306 Office Action with English Translation, Jun. 10, 2009, 4 pages.
Journee et al., "System for Intra-Operative Monitoring of the Cortical Integrity of the Pedicle During Pedicle Screw Placement in Low-Back Surgery: Design and Clinical Results," Sensory and Neuromuscular Diagnostic Instrumentation and Data Analysis I, 18th Annual International Conference on Engineering in Medicine and Biology Society, Amsterdam, 1996, pp. 144-145.
Kossmanm et al., "The use of a retractor system (SynFrame) for open, minimal invasive reconstruction of the anterior column of the thoracic and lumbar spine," Eur Spine J., 2001, 10: 396-402.
Kossmann, et al., Minimally Invasive Vertebral Replacement with Cages in Thoracic and Lumbar Spine, European Journal of Trauma 2001, 27: 292-300.

(56) References Cited

OTHER PUBLICATIONS

Larson and Maiman, "Surgery of the Lumbar Spine," Thieme Medical Publishers, Inc., 1999, pp. 305-319.
Lenke et al., "Triggered Electromyographic Threshold for Accuracy of Pedicle Screw Placement," spine, 1995, 20(4): 1585-1591.
Leu, et al., Percutaneous Fusion of the Lumbar Spine, Spine, 1992, 6(3): 593-604.
Litwin, et al., Hand-assisted laparoscopic surgery (HALS) with the handport system, Annals of Surgery, 2000, 231(5):715-723.
Maguire et al., "Evaluation of Intrapedicular Screw Position Using Intraoperative Evoked Electromyography," Spine 1995, 20(9): 1068-1074.
Marina, "New Technology for Guided Navigation with Real Time Nerve Surveillance for Minimally Invasive Spine Discectomy & Arthrodesis," Spineline 2000, p. 39.
Martin et al. "Initiation of Erection and Semen Release by Rectal Probe Electrostimulation (RPE)," The Journal of Urology, The Williams & Wilkins Co., 1983, 129: 637-642.
Mathews et al., "Laparoscopic Discectomy with Anterior Lumbar Interbody Fusion," SPINE, 1995, 20(16): 1797-1802.
Mayer, "A New Microsurgical Technique for Minimally Invasive Anterior Lumbar Interbody Fusion," Spine, 1997, 22(6): 691-699.
Mayer and Brock, Percutaneous endoscopic discectomy: surgical technique and preliminary results compared to microsurgical discectomy, J. Neurosurg, 1993, 78: 216-225.
Mayer and Wiechert, "Microsurgical Anterior Approaches to the Lumbar Spine for Interbody Fusion and Total Disc Replacement," Neurosurgery, 2002, 51(2): 159-165.
Mayer H. M. (ed.) Minimally Invasive Spine Surgery: A Surgical Manual. 2000. 51 pages.
Mayer "The ALIF Concept," Eur Spine J., 2000, 9(1): S35-S43.
McAfee et al., Minimally Invasive Anterior Retroperitoneal Approach to the Lumbar Spine: Emphasis on the Lateral BAK, Spine, 1998, 23(13): 1476-1484.
MedlinePlus, a Service of the U.S. National Library of Medicine and National Institutes of Health. Available online: http://www.nlm.nih.gov/medlineplus/. Accessed Jul. 11, 2012.
Medtronic Sofamor Danek "METRx System Surgical Technique," 2004, 22 pages.
Medtronic Sofamor Danek "METRx TM MicroDiscectomy System," Medtronic Sofamor Danek USA, 2000, 21 pgs.
Medtronic Sofamor Danek "UNION TM / UNION-L TM Anterior & Lateral Impacted Fusion Devices: Clear choice of stabilization," Medtronic Sofamor Danek, 2000, 4 pages.
Medtronic Sofamor Danek "UNION TM / UNION-L TM Anterior & Lateral Impacted Fusion Devices: Surgical Technique" Medtronic Sofamor Danek, 2001, 20 pages.
Medtronic XOMED Surgical Products, Inc., NIM-Response Nerve Integrity Monitor Intraoperative EMG Monitor User's Guide, Revision B, 2000, 47 pages.
Merriam-Webster's Collegiate Dictionary, p. 65 (10th ed. 1998).
METRx Delivered Order Form, 1999, 13 pages.
"MetRx System MicroEndoscopic Discectomy: An Evolution in Minimally Invasive Spine Surgery," Sofamor Danek, 1999, 6 pages.
Minahan et al., "The Effect of Neuromuscular Blockade on Pedicle Screw Stimulation Thresholds" Spine, Department of Neurology, Johns Hopkins University School of Medicine, Oct. 1, 2000, 25(19): 2526-2530.
Moed, et al., Evaluation of Intraoperative Nerve-Monitoring During Insertion of an Iliosacral Implant in an Animal Model, Journal of Bone and Joint Surgery, 1999, 81-A(II):9.
"Neurovision SE Nerve Locator/Monitor", RLN Systems Inc. Operators Manual, 1999,22 pages.
Notice of Allowance dated Mar. 30, 2017 for U.S. Appl. No. 14/263,797.
Notice of Allowance dated Apr. 12, 2017 for U.S. Appl. No. 15/272,071.
Notice of Allowance in U.S. Appl. No. 11/789,284, dated Jul. 18, 2011, 8 pages.
NuVasive 51O(k) Premarket Notification: Neurovision JJB System (Device Description), Aug. 20, 2007, 8 pages.
NuVasive 510(k) Premarket Notification: Spinal System (Summary), Apr. 12, 2004, 10 pages.
NuVasive 51O(k) Summary NIM Monitor, Sep. 4, 1998, 4 pages.
NuVasive correspondence re 51O(k) Premarket Notification INS-1 Intraoperative Nerve Surveillance System: Section IV Device Description, pp. 12-51 (prior to Sep. 25, 2003).
NuVasive, Inc's Opening Claim Construction Brief Regarding U.S. Pat. No. 8,000,782; 472 8,005,535; 8,016,767; 8,192,356; 8,187,334; 8,361,156; D652,922; and 5,676,146 C2, filed Sep. 3, 2013, in *Warsaw Orthopedic, Inc.* v. *NuVasive, Inc.*, No. 3:12-cv-02738-CAB-MDD (S.D. Cal.)., 34 pages.
*NuVasive, Inc.* v. *Medtronic, Inc.* in 15-1674 filed May 26, 2015, Individual documents of the referenced court case are not being submitted herewith, as Applicant understands the documents to be readily accessible by the Examiner. However, Applicant can provide any of the documents upon request.
*NuVasive, Inc.* v. *Medtronic, Inc.* in 15-1712 filed Jun. 8, 2015, Individual documents of the referenced court case are not being submitted herewith, as Applicant understands the documents to be readily accessible by the Examiner. However, Applicant can provide any of the documents upon request.
*NuVasive, Inc.* v. *Warsaw Orthopedic, Inc.* in 15-1049 filed Oct. 14, 2014, Individual documents of the referenced court case are not being submitted herewith, as Applicant understands the documents to be readily accessible by the Examiner. However, Applicant can provide any of the documents upon request.
NuVasive "INS-1 Screw Test," 2001, 10 pages.
NuVasive letter re: 51O(k) for Neurovision JJB System (Summary), Sep. 25, 2001, 28 pages.
NuVasive letter re 51Ok Guided Arthroscopy System, Oct. 5, 1999, 6 pages.
NuVasive letter re 51Ok INS-1 Intraoperative Nerve Surveillance System, Nov. 13, 2000, 7 pages.
NuVasive letter re 51Ok Neuro Vision JJB System, Oct. 16, 2001, 5 pages.
NuVasive letter re: 51O(k) Premarket Notification: Guided Spinal Arthroscopy System (Device Description), Feb. 1, 1999, 40 pages.
NuVasive letter re: 51O(k) Premarket Notification: Neurovision JJB System (Device Description), Jun. 24, 2005, 16 pages.
NuVasive letter re: Special 51O(k) Premarket Notification: Neurovision JJB System (Device Description), Jul. 3, 2003, 18 pages.
NuVasive letter re: Special 51O(k) Premarket Notification: Neurovision JJB System (Device Description), Mar. 1, 2004, 16 pages.
NuVasive letter re: Special 51O(k) Premarket Notification: Neurovision JJB System (Device Description), May 26, 2005, 17 pages.
NuVasive letter re: Special 51O(k) Premarket Notification: Neurovision JJB System (Device Description), Sep. 14, 2006, 17 pages.
NuVasive's spine surgery system cleared in the US, Pharm & Medical Industry Week, Dec. 10, 2001, 1 page.
NuVasive Triad TM Cortical Bone Allograft, 2000, 1 page (prior to Sep. 25, 2003).
NuVasive Triad TM Tri-Columnar Spinal EndoArthrodesis TM via Minimally Invasive Guidance, 2000, 1 page (prior to Sep. 25, 2003).
NuVasive Vector TM Cannulae, 2000, 1 page.
NuVasive Vertebral Body Access System, 2000, 1 page.
NuVasiveTM Receives Clearance to Market Two Key Elem Minimally Invasive Spine Surgery System, Nov. 27, 2001, 20 pages.
"Sofamor Danek MED Microendoscopic Discectomy System Brochure" including Rapp "New endoscopic lumbar technique improves access preserves tissue" Reprinted with permission from: Orthopedics Today. 1998, 18(1):2 pages.
Office Action dated Jan. 11, 2012 for U.S. Appl. No. 11/982,185.
Office Action dated Jan. 12, 2012 for U.S. Appl. No. 11/489,020.
Office Action dated Jan. 21, 2011 for U.S. Appl. No. 11/982,185.
Office Action dated Feb. 26, 2016 for U.S. Appl. No. 14/622,585.
Office Action dated Mar. 16, 2009 for U.S. Appl. No. 11/489,020.
Office Action dated Mar. 29, 2017 for U.S. Appl. No. 15/448,395.
Office Action dated Apr. 5, 2017 for U.S. Appl. No. 15/445,854.
Office Action dated Apr. 7, 2017 for U.S. Appl. No. 15/059,215.
Office Action dated Apr. 29, 2010 for U.S. Appl. No. 11/982,185.
Office Action dated May 6, 2010 for U.S. Appl. No. 11/489,020.

(56) References Cited

OTHER PUBLICATIONS

Office Action dated May 8, 2014 for U.S. Appl. No. 13/964,836.
Office Action dated Jun. 17, 2009 for U.S. Appl. No. 11/982,185.
Office Action dated Sep. 15, 2008 for U.S. Appl. No. 11/489,020.
Office Action dated Sep. 19, 2016 for U.S. Appl. No. 14/263,797.
Office Action dated Sep. 23, 2016 for U.S. Appl. No. 14/622,585.
Office Action dated Oct. 9, 2009 for U.S. Appl. No. 11/489,020.
Office Action dated Oct. 20, 2016 for U.S. Appl. No. 14/297,369.
Office Action dated Nov. 28, 2016 for U.S. Appl. No. 14/994,640.
Office Action dated Nov. 4, 2016 for U.S. Appl. No. 14/297,438.
Office Action dated Dec. 19, 2014 for U.S. Appl. No. 13/964,836.
Office action from U.S. Appl. No. 11/789,284, dated Feb. 7, 2011, 10 pages.
Patent Owner NuVasive Inc's Preliminary Response from IPR2014-00034, dated Jan. 15, 2014, 66 pages.
Patent Owner NuVasive Inc's Preliminary Response from IPR2014-00035, dated Jan. 15, 2014, 42 pages.
Patent Owner NuVasive Inc's Preliminary Response from IPR2014-00073, dated Jan. 31, 2014, 2014, 46 pages.
Patent Owner NuVasive Inc's Preliminary Response from IPR2014-00074, dated Jan. 31, 2014, 68 pages.
Patent Owner NuVasive Inc's Preliminary Response from IPR2014-00075, dated Jan. 31, 2014, 54 pages.
Patent Owner NuVasive Inc's Preliminary Response from IPR2014-00076, dated Jan. 31, 2014, 58 pages.
Patent Owner NuVasive Inc's Preliminary Response from IPR2014-00081, dated Jan. 31, 2014, 47 pages.
Patent Owner NuVasive Inc's Preliminary Response from IPR2014-00087, dated Jan. 31, 2014, 51 pages.
Patent Trial and Appeal Board Decision from IPR 2014-00034, dated Apr. 8, 2014, 35 pages.
Patent Trial and Appeal Board Decision from IPR 2014-00035, dated Apr. 8, 2014, 12 pages.
Patent Trial and Appeal Board Decision from IPR 2014-00073, dated Apr. 8, 2014, 34 pages.
Patent Trial and Appeal Board Decision from IPR 2014-00074, dated Apr. 8, 2014, 28 pages.
Patent Trial and Appeal Board Decision from IPR 2014-00075, dated Apr. 8, 2014, 23 pages.
Patent Trial and Appeal Board Decision from IPR 2014-00076, dated Apr. 8, 2014, 11 pages.
Patent Trial and Appeal Board Decision from IPR 2014-00081, dated Apr. 8, 2014, 31 pages.
Patent Trial and Appeal Board Decision from IPR 2014-00087, dated Apr. 8, 2014, 31 pages. Individual documents of the referenced court case are not being submitted herewith, as Applicant understands the documents to be readily accessible by the Examiner. However, Applicant can provide any of the documents upon request.
Petition for Inter Partes Review by Medtronic, Inc. in IPR2013-00504 filed Aug. 14, 2013, Individual documents of the referenced court case are not being submitted herewith, as Applicant understands the documents to be readily accessible by the Examiner. However, Applicant can provide any of the documents upon request.
Petition for Inter Partes Review by Medtronic, Inc. in IPR2013-00506 filed Aug. 14, 2013, Individual documents of the referenced court case are not being submitted herewith, as Applicant understands the documents to be readily accessible by the Examiner. However, Applicant can provide any of the documents upon request.
Petition for Inter Partes Review by Medtronic, Inc. in IPR2013-00507 filed Aug. 14, 2013, Individual documents of the referenced court case are not being submitted herewith, as Applicant understands the documents to be readily accessible by the Examiner. However, Applicant can provide any of the documents upon request.
Petition for Inter Partes Review by Medtronic, Inc. in IPR2013-00508 filed Aug. 14, 2013, Individual documents of the referenced court case are not being submitted herewith, as Applicant understands the documents to be readily accessible by the Examiner. However, Applicant can provide any of the documents upon request.
Petition for Inter Partes Review by Medtronic, Inc. in IPR2014-00034 filed Oct. 8, 2013, Individual documents of the referenced court case are not being submitted herewith, as Applicant understands the documents to be readily accessible by the Examiner. However, Applicant can provide any of the documents upon request.
Petition for Inter Partes Review by Medtronic, Inc. in IPR2014-00035 filed Oct. 8, 2013, Individual documents of the referenced court case are not being submitted herewith, as Applicant understands the documents to be readily accessible by the Examiner. However, Applicant can provide any of the documents upon request.
Petition for Inter Partes Review by Medtronic, Inc. in IPR2014-00071 filed Oct. 16, 2013, Individual documents of the referenced court case are not being submitted herewith, as Applicant understands the documents to be readily accessible by the Examiner. However, Applicant can provide any of the documents upon request.
Petition for Inter Partes Review by Medtronic, Inc. in IPR2014-00487 filed Mar. 5, 2014, Individual documents of the referenced court case are not being submitted herewith, as Applicant understands the documents to be readily accessible by the Examiner. However, Applicant can provide any of the documents upon request.
Petition for Inter Partes Review by NuVasive, Inc. in IPR2013-00206 filed Mar. 22, 2013, Individual documents of the referenced court case are not being submitted herewith, as Applicant understands the documents to be readily accessible by the Examiner. However, Applicant can provide any of the documents upon request.
Petition for Inter Pates Review by NuVasive, Inc. in IPR2013-00208 filed Mar. 22, 2013, Individual documents of the referenced court case are not being submitted herewith, as Applicant understands the documents to be readily accessible by the Examiner. However, Applicant can provide any of the documents upon request.
Petition for Inter Partes Review by NuVasive, Inc. in IPR2013-00395 filed Jun. 27, 2013, Individual documents of the referenced court case are not being submitted herewith, as Applicant understands the documents to be readily accessible by the Examiner. However, Applicant can provide any of the documents upon request.
Petition for Inter Partes Review by NuVasive, Inc. in IPR2013-00396 filed Jun. 27, 2013, Individual documents of the referenced court case are not being submitted herewith, as Applicant understands the documents to be readily accessible by the Examiner. However, Applicant can provide any of the documents upon request.
Petition for Inter Partes Review by NuVasive, Inc. in IPR2015-00502 filed Dec. 24, 2014, Individual documents of the referenced court case are not being submitted herewith, as Applicant understands the documents to be readily accessible by the Examiner. However, Applicant can provide any of the documents upon request.
Pimenta, et al., Implante de protese de nucleo pulposo: analise inicial, Journal Brasileiro de Neurocirurgia, 2001, 12(2): 93-96.
Pimenta et al., The Lateral Endoscopic Transpsoas Retroperitoneal Approach (Letra) for Implants in the Lumbar Spine, World Spine II—Second Interdisciplinary Congress on Spine Care, Aug. 2003, 2 pages.
Pimenta, Initial Clinical Results of Direct Lateral, Minimally Invasive Access to the Lumbar Spine for Disc Nucleus Replacement Using a Novel Neurophysiological Monitoring System, The 9th /MAST, May, 2002, 1 page.
Pither et al., "The Use of Peripheral Nerve Stimulators for Regional Anesthesia: Review of Experimental Characteristics Technique and Clinical Applications," Regional Anesthesia, 1985, 10:49-58.
Plaintiffs' Preliminary Invalidity Contentions re U.S. Pat. Nos. 7,207,949; 7,470,236 and 7,582,058, Sep. 18,2009, 19 pages.
Plaintiffs' Preliminary Invalidity Contentions-Appendices, Sep. 18, 2009, 191 pages.
Plaintiffs' Supplemental Preliminary Invalidity Contentions re U.S. Pat. Nos. 7,207,949, 7,470,236, and 7,582,058, Sep. 29, 2009, 21 pages.
Plaintiffs' Supplemental Preliminary Invalidity Contentions-Appendices, Sep. 29, 2009, 294 pages.
Raj et al., "Infraclavicular Brachia! Plexus Block—A New Approach" Anesthesia and Analgesia, 1973, (52)6: 897-904.
Raj et al., "The Use of Peripheral Nerve Stimulators for Regional Anesthesia," Clinical Issues in Regional Anesthesia 1985, 1(4):1-6.
Raj et al., "Use of the Nerve Stimulator for Peripheral Blocks," Regional Anesthesia, Apr.-Jun. 1980, pp. 14-21.

(56) References Cited

OTHER PUBLICATIONS

Rao, et al. "Dynamic retraction of the psoas muscle to expose the lumbar spine using the retroperitoneal approach," J. Neurosurg Spine, 2006, 5: 468-470.
Request for Inter Partes Reexamination in re: U.S. Pat. No. 7,691,057, dated Feb. 8, 2012, 50 pages.
Request for Inter Partes Reexamination in re U.S. Pat. No. 7,905,840, dated Feb. 8, 2012, 204 pages.
Request for Inter PartesReexamination in re U.S. Pat. No. 7,819,801, dated Feb. 8, 2012, 89 pages.
Rose et al., "Persistently Electrified Pedicle Stimulation Instruments in Spinal Instrumentation: Techniques and Protocol Development," SPINE, 1997, 22(3): 334-343.
Rosenthal, et al., Removal of a Protruded Thoracic Disc Using Microsurgical Endoscopy, Spine, 1994, 19(9): 1087-1091.
Schaffer and Kambin, Percutaneous Posterolateral Lumbar Discectomy and Decompression with a 6.9-Millimeter Cannula, The Journal of Bone and Joint Surgery, 1991, 73A(6): 822-831.
Schick et al., "Microendoscopic lumbar discectomy versus open surgery: an intraoperative EMG study," Eur Spine J, 2002, 11: 20-26.
Shafik, "Cavernous Nerve Simulation through an Extrapelvic Subpubic Approach: Role in Penile Erection," Eur. Ural, 1994,26: 98-102.
Smith and Foley "MetRx System MicroEndoscopic Discectomy: Surgical Technique" Medtronic Sofamor Danek, 2000, 24 pages.
"The Brackmann II EMG Monitoring System," Medical Electronics Co. Operator's Manual Version 1.1, 1995, 50 pages.
"The Nicolet Viking IV," Nicolet Biomedical Products, 1999, 6 pages.
Toleikis et al., "The Usefulness of Electrical Stimulation for Assessing Pedicle Screw Replacements," Journal of Spinal Disorder 2000, 13(4): 283-289.
Traynelis, Spinal Arthroplasty, Neurological Focus, 2002, 13(2): 12 pages.
U.S. Appl. No. 60/325,424, filed Sep. 25, 2001, 346 pages.
U.S. Appl. No. 60/392,214, filed Jun. 26, 2002, 97 pages.
*Warsaw Orthopedic, Inc. v. NuVasive, Inc.* in 12-1263 filed Mar. 15, 2012.
*Warsaw Orthopedic, Inc. v. NuVasive, Inc.* in 12-1266 filed Mar. 15, 2012.
*Warsaw Orthopedic, Inc. v. NuVasive, Inc.* in 13-1576 filed Aug. 21, 2013.
*Warsaw Orthopedic, Inc. v. NuVasive, Inc.* in 13-1577 filed Aug. 21, 2013.
Wolfa et al., "Retroperitoneal lateral lumbar interbody fusion with titanium threaded fusion cages," J. Neurosurg (Spine 1), 2002, 96: 50-55.
Zdeblick, Thomas A. (ed.). Anterior Approaches to the Spine. 1999. 43 pages.
INS-1 Guide Dec. 31, 2000, Part I.
INS-1 Guide Dec. 31, 2000, Part II.
INS-1 Guide Dec. 31, 2000, Part III.

* cited by examiner

SURGICAL ACCESS SYSTEM AND RELATED METHODS

CROSS-REFERENCES TO RELATED APPLICATIONS

This application is a continuation of U.S. patent application Ser. No. 15/439,889, pending, filed Feb. 22, 2017, which is a continuation of U.S. patent application Ser. No. 14/598,043 (now U.S. Pat. No. 9,610,071), filed Jan. 15, 2015, which is a continuation of U.S. patent application Ser. No. 14/299,800 (now U.S. Pat. No. 8,942,801), filed Jun. 9, 2014, which is a continuation of Ser. No. 14/052,271 (now U.S. Pat. No. 8,764,649), filed on Oct. 11, 2013, which is a continuation of U.S. patent application Ser. No. 13/742,268 (now U.S. Pat. No. 8,556,808), filed on Jan. 15, 2013, which is a continuation of U.S. patent application Ser. No. 12/623,016 (now U.S. Pat. No. 8,355,780), filed on Nov. 20, 2009, which is a division of U.S. patent application Ser. No. 11/789,284 (now U.S. Pat. No. 8,016,767), filed on Apr. 23, 2007, which is a continuation of U.S. patent application Ser. No. 11/137,169 (now U.S. Pat. No. 7,207,949), filed on May 25, 2005, which is a continuation of PCT Application Serial No. PCT/US04/31768, filed Sep. 27, 2004, which claims the benefit of priority from U.S. Provisional Patent Application Ser. No. 60/506,136, filed Sep. 25, 2003, the entire contents of which are hereby expressly incorporated by reference into this disclosure as if set forth fully herein.

The present application also incorporates by reference the following commonly owned patent applications in their entireties: PCT App. Ser. No. PCT/US02/22247, entitled "System and Methods for Determining Nerve Proximity, Direction, and Pathology During Surgery," filed on Jul. 11, 2002; PCT App. Ser. No. PCT/US02/30617, entitled "System and Methods for Performing Surgical Procedures and Assessments," filed on Sep. 25, 2002; PCT App. Ser. No. PCT/US02/35047, entitled "System and Methods for Performing Percutaneous Pedicle Integrity Assessments," filed on Oct. 30, 2002; and PCT App. Ser. No. PCT/US03/02056, entitled "System and Methods for Determining Nerve Direction to a Surgical Instrument," filed Jan. 15, 2003 (collectively "Neuro Vision PCT Applications").

BACKGROUND OF THE INVENTION

1. Field of the Invention

The present invention relates generally to systems and methods for performing surgical procedures and, more particularly, for accessing a surgical target site in order to perform surgical procedures.

2. Background of the Prior Art

A noteworthy trend in the medical community is the move away from performing surgery via traditional "open" techniques in favor of minimally invasive or minimal access techniques. Open surgical techniques are generally undesirable in that they typically require large incisions and high amounts of tissue displacement to gain access to the surgical target site, which produces concomitantly high amounts of pain, lengthened hospitalization (increasing health care costs), and high morbidity in the patient population. Less-invasive surgical techniques (including so-called "minimal access" and "minimally invasive" techniques) are gaining favor due to the fact that they involve accessing the surgical target site via incisions of substantially smaller size with greatly reduced tissue displacement requirements. This, in turn, reduces the pain, morbidity and cost associated with such procedures. The access systems developed to date, however, fail in various respects to meet all the needs of the surgeon population.

One drawback associated with prior art surgical access systems relates to the ease with which the operative corridor can be created, as well as maintained over time, depending upon the particular surgical target site. For example, when accessing surgical target sites located beneath or behind musculature or other relatively strong tissue (such as, by way of example only, the psoas muscle adjacent to the spine), it has been found that advancing an operative corridor-establishing instrument directly through such tissues can be challenging and/or lead to unwanted or undesirable effects (such as stressing or tearing the tissues). While certain efforts have been undertaken to reduce the trauma to tissue while creating an operative corridor, such as (by way of example only) the sequential dilation system of U.S. Pat. No. 5,792,044 to Foley et al., these attempts are nonetheless limited in their applicability based on the relatively narrow operative corridor. More specifically, based on the generally cylindrical nature of the so-called "working cannula," the degree to which instruments can be manipulated and/or angled within the cannula can be generally limited or restrictive, particularly if the surgical target site is a relatively deep within the patient.

Efforts have been undertaken to overcome this drawback, such as shown in U.S. Pat. No. 6,524,320 to DiPoto, wherein an expandable portion is provided at the distal end of a cannula for creating a region of increased cross-sectional area adjacent to the surgical target site. While this system may provide for improved instrument manipulation relative to sequential dilation access systems (at least at deep sites within the patient), it is nonetheless flawed in that the deployment of the expandable portion may inadvertently compress or impinge upon sensitive tissues adjacent to the surgical target site. For example, in anatomical regions having neural and/or vasculature structures, such a blind expansion may cause the expandable portion to impinge upon these sensitive tissues and cause neural and/or vasculature compromise, damage and/or pain for the patient.

This highlights yet another drawback with the prior art surgical access systems, namely, the challenges in establishing an operative corridor through or near tissue having major neural structures which, if contacted or impinged, may result in neural impairment for the patient. Due to the threat of contacting such neural structures, efforts thus far have largely restricted to establishing operative corridors through tissue having little or substantially reduced neural structures, which effectively limits the number of ways a given surgical target site can be accessed. This can be seen, by way of example only, in the spinal arts, where the exiting nerve roots and neural plexus structures in the psoas muscle have rendered a lateral or far lateral access path (so-called trans-psoas approach) to the lumbar spine virtually impossible. Instead, spine surgeons are largely restricted to accessing the spine from the posterior (to perform, among other procedures, posterior lumbar interbody fusion (PLIF)) or from the anterior (to perform, among other procedures, anterior lumbar interbody fusion (ALIF).

Posterior-access procedures involve traversing a shorter distance within the patient to establish the operative corridor, albeit at the price of oftentimes having to reduce or cut away part of the posterior bony structures (i.e. lamina, facets, spinous process) in order to reach the target site (which typically comprises the disc space). Anterior-access procedures are relatively simple for surgeons in that they do not involve reducing or cutting away bony structures to reach the surgical target site. However, they are nonetheless disadvantageous in that they require traversing through a much greater distance within the patient to establish the operative corridor, oftentimes requiring an additional surgeon to assist with moving the various internal organs out of the way to create the operative corridor.

The present invention is directed at eliminating, or at least minimizing the effects of, the above-identified drawbacks in the prior art.

SUMMARY OF THE INVENTION

The present invention accomplishes this goal by providing a novel access system and related methods which involve detecting the existence of (and optionally the distance and/or direction to) neural structures before, during, and after the establishment of an operative corridor through (or near) any of a variety of tissues having such neural structures which, if contacted or impinged, may otherwise result in neural impairment for the patient. It is expressly noted that, although described herein largely in terms of use in spinal surgery, the access system of the present invention is suitable for use in any number of additional surgical procedures wherein tissue having significant neural structures must be passed through (or near) in order to establish an operative corridor.

According to one broad aspect of the present invention, the access system comprises a tissue distraction assembly and a tissue retraction assembly, both of which may be equipped with one or more electrodes for use in detecting the existence of (and optionally the distance and/or direction to) neural structures. The tissue distraction assembly (in conjunction with one or more elements of the tissue retraction assembly) is capable of, as an initial step, distracting a region of tissue between the skin of the patient and the surgical target site. The tissue retraction assembly is capable of, as a secondary step, being introduced into this distracted region to thereby define and establish the operative corridor. Once established, any of a variety of surgical instruments, devices, or implants may be passed through and/or manipulated within the operative corridor depending upon the given surgical procedure. The electrode(s) are capable of, during both tissue distraction and retraction, detecting the existence of (and optionally the distance and/or direction to) neural structures such that the operative corridor may be established through (or near) any of a variety of tissues having such neural structures which, if contacted or impinged, may otherwise result in neural impairment for the patient. In this fashion, the access system of the present invention may be used to traverse tissue that would ordinarily be deemed unsafe or undesirable, thereby broadening the number of manners in which a given surgical target site may be accessed.

The tissue distraction assembly may include any number of components capable of performing the necessary distraction. By way of example only, the tissue distraction assembly may include a K-wire, an initial dilator of split construction, and one or more dilators of traditional (that is, nonsplit) construction for performing the necessary tissue distraction to receive the remainder of the tissue retractor assembly thereafter. One or more electrodes may be provided on one or more of the K-wire and dilator(s) to detect the presence of (and optionally the distance and/or direction to) neural structures during tissue distraction.

The tissue retraction assembly may include any number of components capable of performing the necessary retraction. By way of example only, the tissue retraction assembly may include one or more retractor blades extending from a handle assembly. The handle assembly may be manipulated to open the retractor assembly; that is, allowing the retractor blades to separate from one another (simultaneously or sequentially) to create an operative corridor to the surgical target site. In a preferred embodiment, this is accomplished by maintaining a posterior retractor blade in a fixed position relative to the surgical target site (so as to avoid having it impinge upon any exiting nerve roots near the posterior elements of the spine) while the additional retractor blades (i.e. cephalad-most and caudal-most blades) are moved or otherwise translated away from the posterior retractor blade (and each other) so as to create the operative corridor in a fashion that doesn't infringe upon the region of the exiting nerve roots.

The retractor blades may be optionally dimensioned to receive and direct a rigid shim element to augment the structural stability of the retractor blades and thereby ensure the operative corridor, once established, will not decrease or become more restricted, such as may result if distal ends of the retractor blades were permitted to "slide" or otherwise move in response to the force exerted by the displaced tissue. In a preferred embodiment, only the posterior retractor blade is equipped with such a rigid shim element. In an optional aspect, this shim element may be advanced into the disc space after the posterior retractor blade is positioned, but before the retractor is opened into the fully retracted position. The rigid shim element is preferably oriented within the disc space such that is distracts the adjacent vertebral bodies, which serves to restore disc height. It also preferably advances a sufficient distance within the disc space (preferably past the midline), which serves the dual purpose of preventing post-operative scoliosis and forming a protective barrier (preventing the migration of tissue (such as nerve roots) into the operative field and the inadvertent advancement of instruments outside the operative field).

The retractor blades may optionally be equipped with a mechanism for transporting or emitting light at or near the surgical target site to aid the surgeon's ability to visualize the surgical target site, instruments and/or implants during the given surgical procedure. According to one embodiment, this mechanism may comprise, but need not be limited to, coupling one or more light sources to the retractor blades such that the terminal ends are capable of emitting light at or near the surgical target site. According to another embodiment, this mechanism may comprise, but need not be limited to, constructing the retractor blades of suitable material (such as clear polycarbonate) and configuration such that light may be transmitted generally distally through the walls of the retractor blade light to shine light at or near the surgical target site. This may be performed by providing the retractor blades having light-transmission characteristics (such as with clear polycarbonate construction) and transmitting the light almost entirely within the walls of the retractor blade (such as by frosting or otherwise rendering opaque portions of the exterior and/or interior) until it exits a portion along the interior (or medially-facing) surface of the retractor blade to shine at or near the surgical target site. The exit portion may be optimally configured such that the light is directed towards the approximate center of the surgical target site and may be provided along the entire inner periphery of the retractor blade or one or more portions therealong.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DESCRIPTION THE PREFERRED EMBODIMENT

Figure 1:
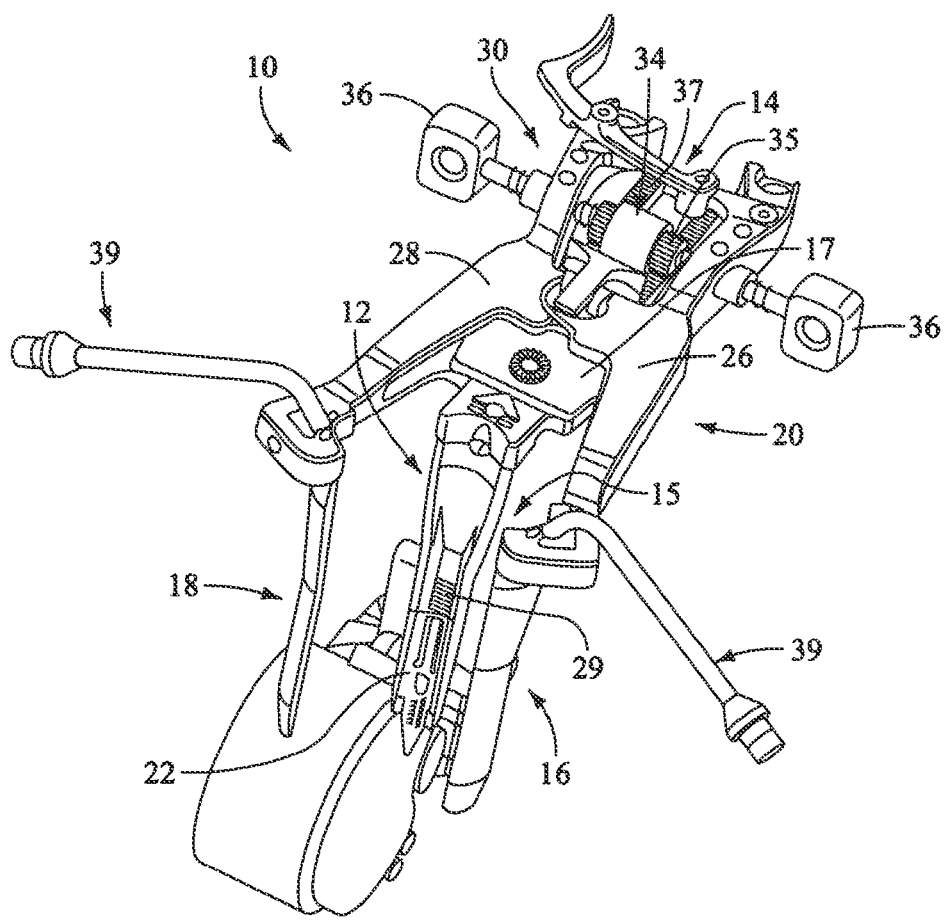
FIG. 1 is a perspective view of a tissue retraction assembly (in use) forming part of a surgical access system according to the present invention.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. It is furthermore to be readily understood that, although discussed below primarily within the context of spinal surgery, the surgical access system of the present invention may be employed in any number of anatomical settings to provide access to any number of different surgical target sites throughout the body. The surgical access system disclosed herein boasts a variety of inventive features and components that warrant patent protection, both individually and in combination.

The present invention involves accessing a surgical target site in a fashion less invasive than traditional "open" surgeries and doing so in a manner that provides access in spite of the neural structures required to be passed through (or near) in order to establish an operative corridor to the surgical target site. Generally speaking, the surgical access system of the present invention accomplishes this by providing a tissue distraction assembly and a tissue retraction assembly, both of which may be equipped with one or more electrodes for use in detecting the existence of (and optionally the distance and/or direction to) neural structures.

These electrodes are preferably provided for use with a nerve surveillance system such as, by way of example, the type shown and described in the co-pending and commonly assigned NeuroVision PCT Applications referenced above, the entire contents of which are expressly incorporated by reference as if set forth herein in their entirety. Generally speaking, this nerve surveillance system is capable of detecting the existence of (and optionally the distance and/or direction to) neural structures during the distraction and retraction of tissue by detecting the presence of nerves by applying a stimulation signal to such instruments and monitoring the evoked EMG signals from the myotomes associated with the nerves being passed by the distraction and retraction systems of the present invention. In so doing, the system as a whole (including the surgical access system of the present invention) may be used to form an operative corridor through (or near) any of a variety of tissues having such neural structures, particularly those which, if contacted or impinged, may otherwise result in neural impairment for the patient. In this fashion, the access system of the present invention may be used to traverse tissue that would ordinarily be deemed unsafe or undesirable, thereby broadening the number of manners in which a given surgical target site may be accessed.

The tissue distraction assembly of the present invention (comprising a K-wire, an initial dilator, and a split-dilator disposed within the initial dilator) is employed to distract the tissues extending between the skin of the patient and a given surgical target site (preferably along the posterior region of the target intervertebral disc). A secondary distraction assembly (i.e. a plurality of sequentially dilating cannulae) may optionally be employed after the initial distraction assembly to further distract the tissue. Once distracted, the resulting void or distracted region within the patient is of sufficient size to accommodate a tissue retraction assembly of the present invention. More specifically, the tissue retraction assembly (comprising a plurality of retractor blades extending from a handle assembly) may be advanced relative to the secondary distraction assembly such that the retractor blades, in a first, closed position, are advanced over the exterior of the secondary distraction assembly. At that point, the handle assembly may be operated to move the retractor blades into a second, open or "retracted" position to create an operative corridor to the surgical target site.

According to one aspect of the invention, following (or before) this retraction, a posterior shim element (which is preferably slideably engaged with the posterior retractor blade) may be advanced such that a distal shim extension in positioned within the posterior region of the disc space. If done before retraction, this helps ensure that the posterior retractor blade will not move posteriorly during the retraction process, even though the other retractor blades (i.e. cephalad-most and caudal-most) are able to move and thereby create an operative corridor. Fixing the posterior retractor blade in this fashion serves several important functions. First, the distal end of the shim element serves to distract the adjacent vertebral bodies, thereby restoring disc height. It also rigidly couples the posterior retractor blade in fixed relation relative to the vertebral bodies. The posterior shim element also helps ensure that surgical instruments employed within the operative corridor are incapable of being advanced outside the operative corridor, preventing inadvertent contact with the exiting nerve roots during the surgery. Once in the appropriate retracted state, the cephalad-most and caudal-most retractor blades may be locked in position and, thereafter, retractor extenders advanced therealong to prevent the ingress or egress of instruments or biological structures (i.e. nerves, vasculature, etc. . . . ) into or out of the operative corridor. Once the operative corridor is established, any of a variety of surgical instruments, devices, or implants may be passed through and/or manipulated within the operative corridor depending upon the given surgical procedure.

FIG. 1 illustrates a tissue retraction assembly 10 forming part of a surgical access system according to the present invention. The retraction assembly 10 includes a plurality of retractor blades extending from a handle assembly 20. By way of example only, the handle assembly 20 is provided with a first retractor blade 12, a second retractor blade 16, and a third retractor blade 18. The retractor assembly 10 is shown in a fully retracted or "open" configuration, with the retractor blades 12, 16, 18 positioned a distance from one another so as to form an operative corridor 15 there between and extending to a surgical target site (e.g. an annulus of an intervertebral disc). Although shown and described below with regard to the three-bladed configuration, it is to be readily appreciated that the number of retractor blades may be increased or decreased without departing from the scope of the present invention. Moreover, although described and shown herein with reference to a generally lateral approach to a spinal surgical target site (with the first blade 12 being the "posterior" blade, the second blade 16 being the "cephalad-most" blade, and the third blade 18 being the "caudal-most" blade), it will be appreciated that the retractor assembly 10 of the present invention may find use in any number of different surgical approaches, including generally posterior, generally postero-lateral, generally anterior and generally antero-lateral.

Figure 2:
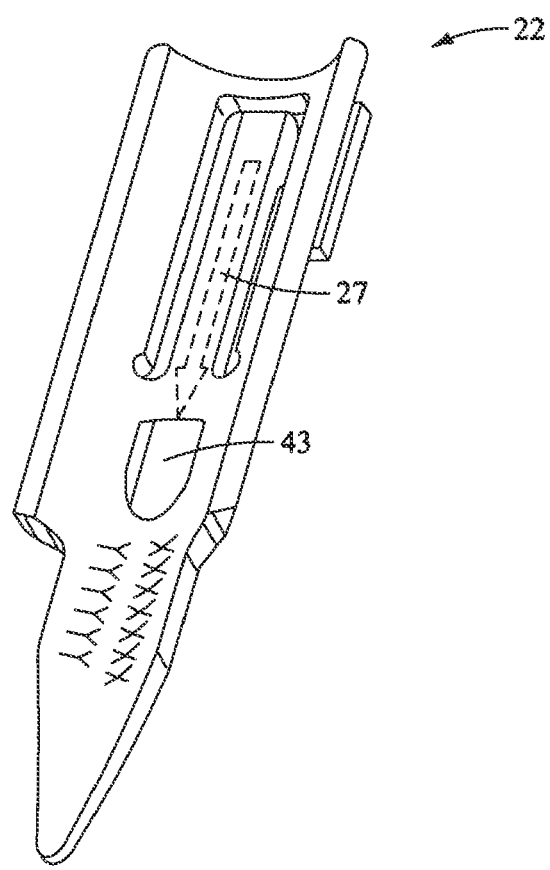
FIGS. 2-3 are perspective views illustrating the front and back of a shim element for use with a posterior retractor blade of the retractor according to the retractor of the present invention.
Figure 3:
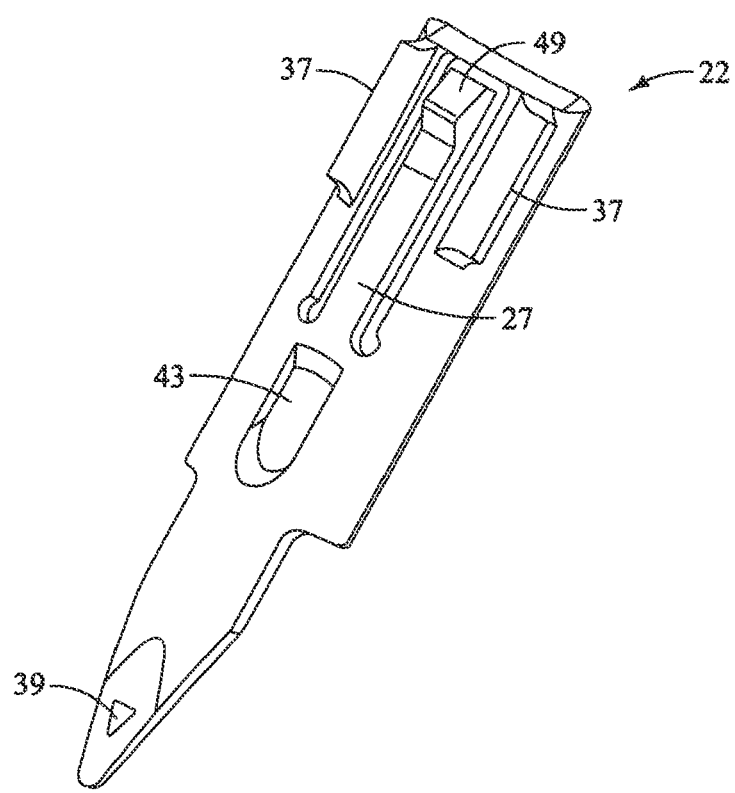
Figure 4:
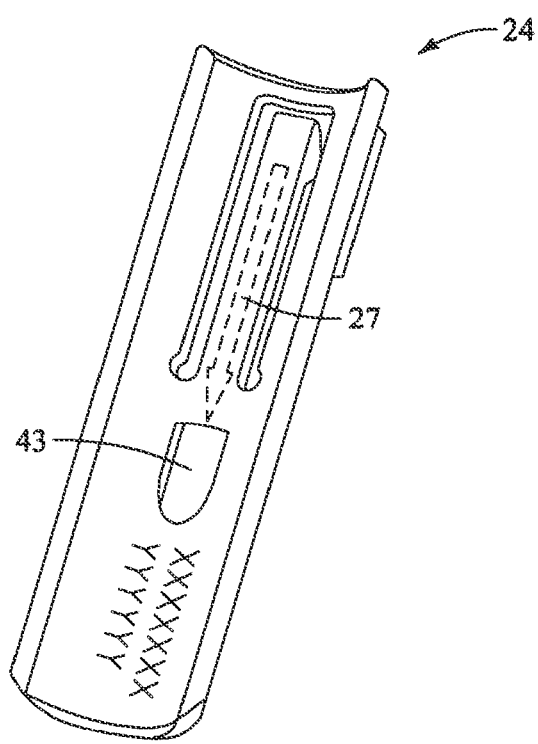
FIGS. 4-5 are perspective views illustrating the front and back of a narrow retractor extender for use with one of a cephalad and caudal retractor blade according to the retractor of the present invention.
Figure 5:
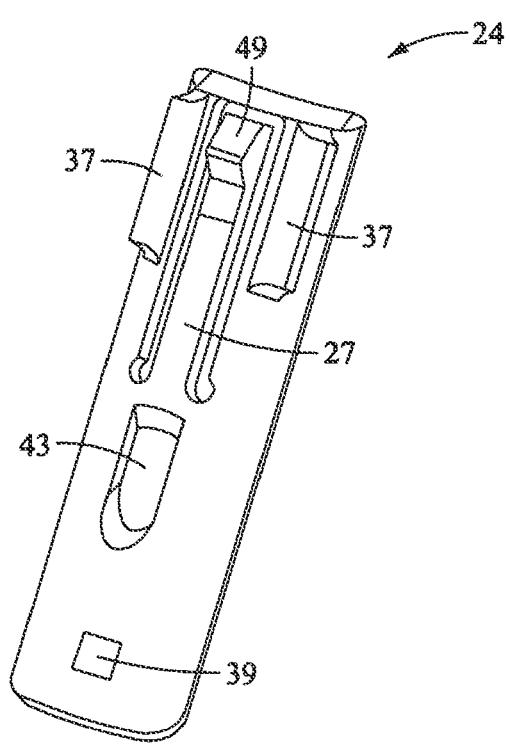
Figure 6:
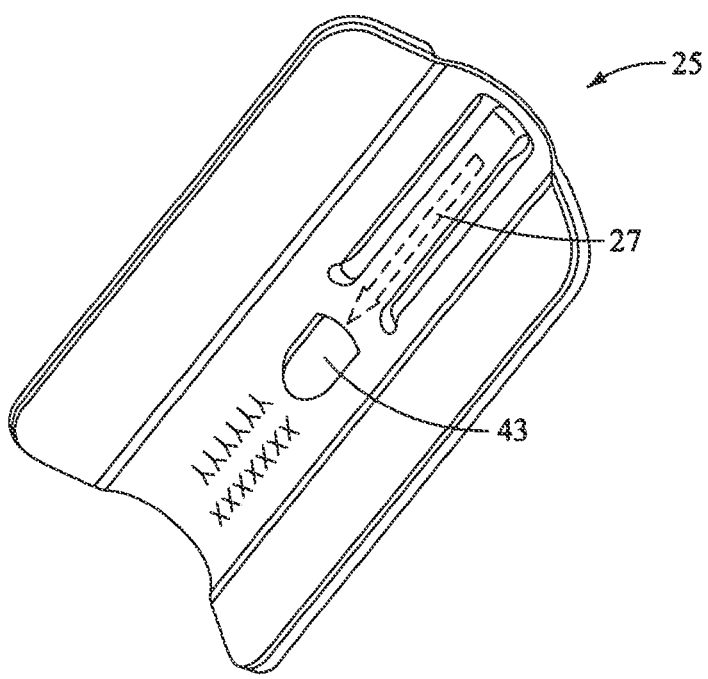
FIGS. 6-7 are perspective views illustrating the front and back of a wide retractor extender for use with one of a cephalad and caudal retractor blade according to the retractor of the present invention.
Figure 7:
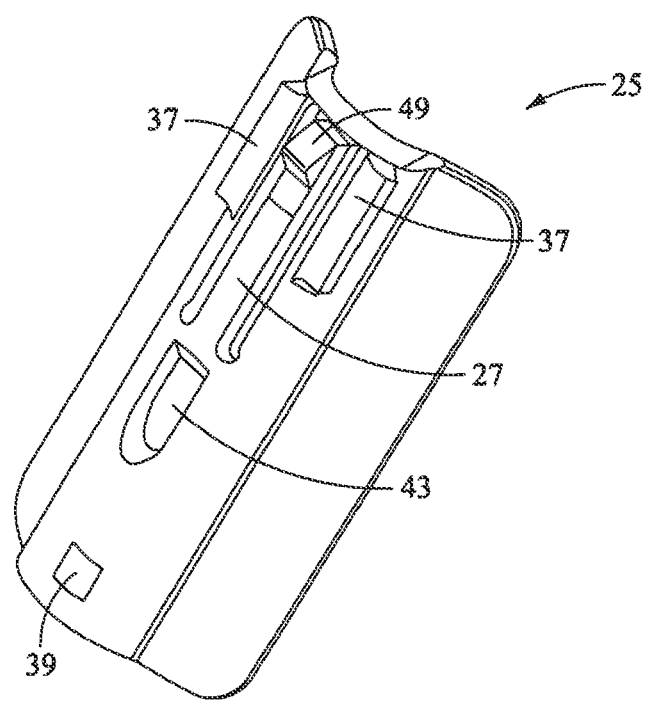

The retractor blades 12, 16, 18 may be equipped with various additional features or components. By way of example only, posterior retractor blade 12 may be equipped with a shim element 22 (shown more clearly in FIGS. 2-3). Shim element 22 serves to distract the adjacent vertebral bodies (thereby restoring disc height), helps secure the retractor assembly 10 relative to the surgical target site, and forms a protective barrier to prevent the ingress or egress of instruments or biological structures (i.e. nerves, vasculature, etc. . . . ) into or out of the operative corridor. Each of the remaining retractor blades (cephalad-most blade 16 and caudal-most blade 18) may be equipped with a refractor extender, such as the narrow refractor extender 24 shown in FIGS. 4-5 or the wide retractor extender 25 shown in FIGS. 6-7. The retractor extenders 24/25 extend from the cephalad-most and caudal-most retractor blades 16, 18 to form a protective barrier to prevent the ingress or egress of instruments or biological structures (i.e. nerves, vasculature, etc. . . . ) into or out of the operative corridor 15.

According to the present invention, any or all of the retractor blades 12, 16, 18, the shim element 22 and/or the retractor extenders 24/25 may be provided with one or more electrodes 39 (preferably at their distal regions) equipped for use with a nerve surveillance system, such as, by way of example, the type shown and described in the NeuroVision PCT Applications. Each of the shim element 22 and/or the retractor extenders 24/25 may also be equipped with a mechanism to selectively and releasably engage with the respective retractor blades 12, 16, 18. By way of example only, this may be accomplished by configuring the shim element 22 and/or the retractor extenders 24/25 with a tab element 27 capable of engaging with corresponding rachet-like grooves (shown at 29 in FIG. 1) along the inner-facing surfaces of the retractor blades 12, 16, 18. Each of the shim element 22 and/or the retractor extenders 24/25 is provided with a pair of engagement elements 37 having, by way of example only, a generally dove-tailed cross-sectional shape. The engagement elements 37 are dimensioned to engage with receiving portions on the respective retractor blades 12, 16, 18. In a preferred embodiment, each of the shim element 22 and/or the retractor extenders 24/25 are provided with an elongate slot 43 for engagement with an insertion tool (not shown). Each tab member 27 is also equipped with an enlarged tooth element 49 which engages within corresponding grooves 29 provided along the inner surface of the retractor blades 12, 16, 18.

The handle assembly 20 may be coupled to any number of mechanisms for rigidly registering the handle assembly 20 in fixed relation to the operative site, such as through the use of an articulating arm mounted to the operating table. The handle assembly 20 includes first and second arm members 26, 28 hingedly coupled via coupling mechanism shown generally at 30. The cephalad-most retractor blade 16 is rigidly coupled (generally perpendicularly) to the end of the first arm member 26. The caudal-most retractor blade 18 is rigidly coupled (generally perpendicularly) to the end of the second arm member 28. The posterior retractor blade 12 is rigidly coupled (generally perpendicularly to) a translating member 17, which is coupled to the handle assembly 20 via a linkage assembly shown generally at 14. The linkage assembly 14 includes a roller member 34 having a pair of manual knob members 36 which, when rotated via manual actuation by a user, causes teeth 35 on the roller member 34 to engage within ratchet-like grooves 37 in the translating member 17. Thus, manual operation of the knobs 36 causes the translating member 17 to move relative to the first and second arm members 26, 28.

Figure 8:
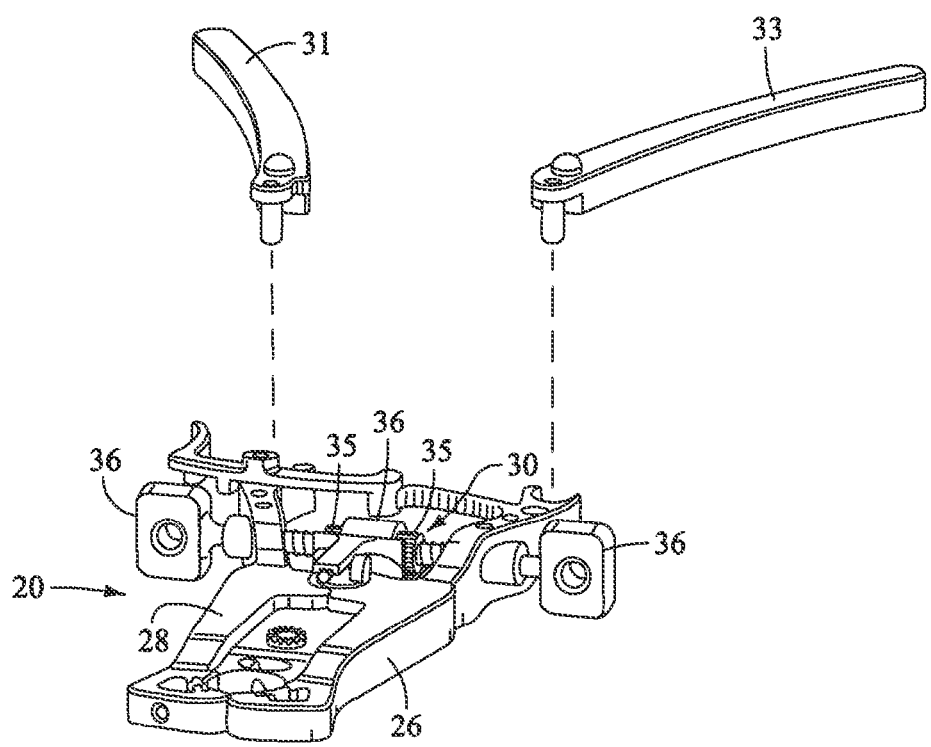
FIG. 8 is a perspective, partially exploded view of the refractor assembly of the present invention, without the retractor blades.

Through the use of handle extenders 31, 33 (FIG. 8), the arms 26, 28 may be simultaneously opened such that the cephalad-most and caudal-most retractor blades 16, 18 move away from one another. In this fashion, the dimension and/or shape of the operative corridor 15 may be tailored depending upon the degree to which the translating member 17 is manipulated relative to the arms 26, 28. That is, the operative corridor 15 may be tailored to provide any number of suitable cross-sectional shapes, including but not limited to a generally circular cross-section, a generally ellipsoidal cross-section, and/or an oval cross-section. Optional light emitting devices 39 may be coupled to one or more of the retractor blades 12, 16, 18 to direct light down the operative corridor 15.

Figure 9:
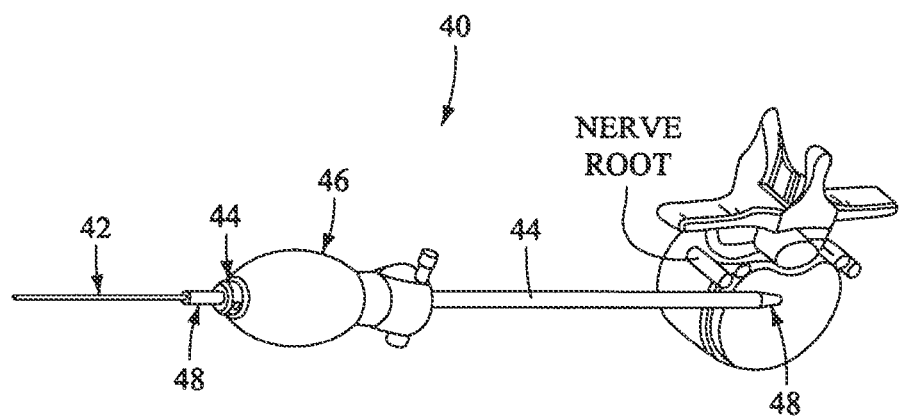
FIG. 9 is a perspective view illustrating the components and use of an initial distraction assembly (i.e. K-wire, an initial dilating cannula with handle, and a split-dilator housed within the initial dilating cannula) forming part of the surgical access system according to the present invention, for use in distracting to a surgical target site (i.e. annulus)
Figure 10:
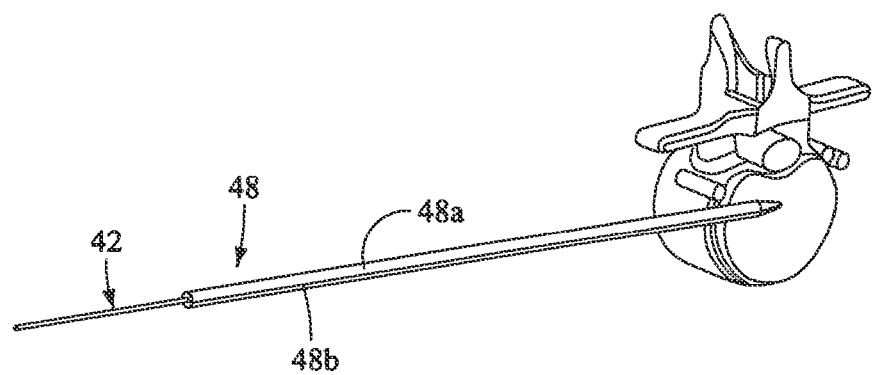
FIG. 10 is a perspective view illustrating the K-wire and split-dilator of the initial distraction assembly with the initial dilating cannula and handle removed.
Figure 11:
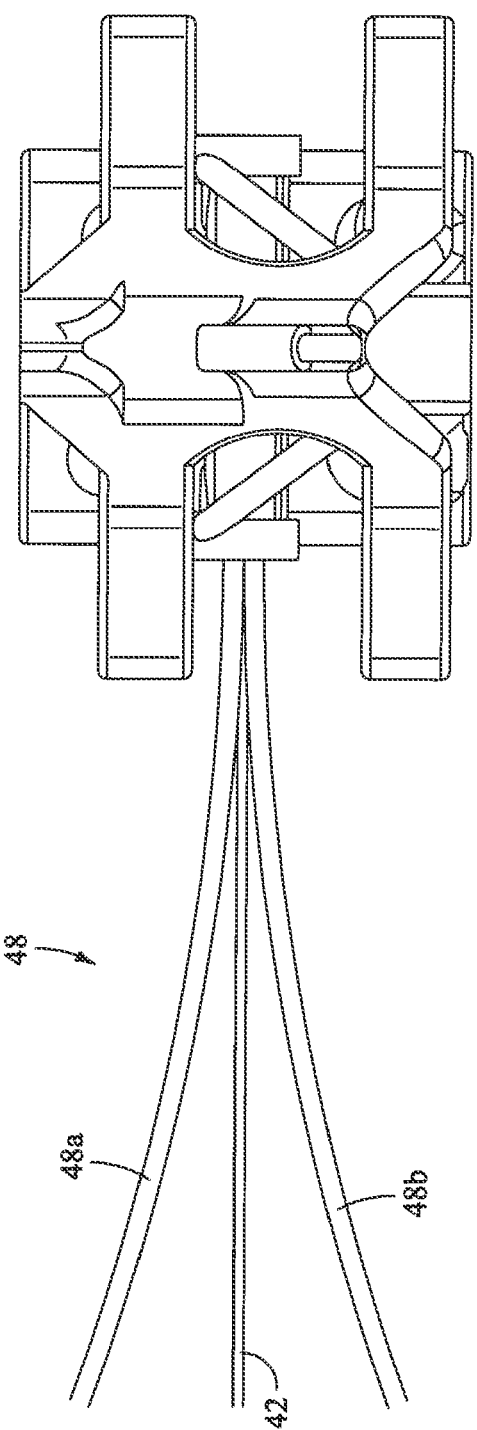
FIG. 11 is a posterior view of the vertebral target site illustrating the split-dilator of the present invention in use distracting in a generally cephalad-caudal fashion according to one aspect of the present invention.

FIG. 9 illustrates an initial distraction assembly 40 forming part of the surgical access system according to the present invention. The initial distraction assembly 40 includes a K-wire 42, an initial dilating cannula 44 with handle 46, and a split-dilator 48 housed within the initial dilating cannula 44. In use, the K-wire 42 and split-dilator 48 are disposed within the initial dilating cannula 44 and the entire assembly 40 advanced through the tissue towards the surgical target site (i.e. annulus). Again, this is preferably accomplished while employing the nerve detection and/or direction features described above. After the initial dilating assembly 40 is advanced such that the distal ends of the split-dilator 48 and initial dilator 44 are positioned within the disc space (FIG. 9), the initial dilator 44 and handle 46 are removed (FIG. 10) to thereby leave the split-dilator 48 and K-wire 42 in place. As shown in FIG. 11, the split-dilator 48 is thereafter split such that the respective halves 48a, 48b are separated from one another to distract tissue in a generally cephalad-caudal fashion relative to the target site. The split dilator 48 may thereafter be relaxed (allowing the dilator halves 48a, 48b to come together) and rotated such that the dilator halves 48a, 48b are disposed in the anterior-posterior plane. Once rotated in this manner, the dilator halves 48a, 48b are again separated to distract tissue in a generally anterior-posterior fashion. Each dilator halve 48a, 48b may be, according to the present invention, provided with one or more electrodes (preferably at their distal regions) equipped for use with a nerve surveillance system, such as, by way of example, the type shown and described in the NeuroVision PCT Applications.

Figure 12:
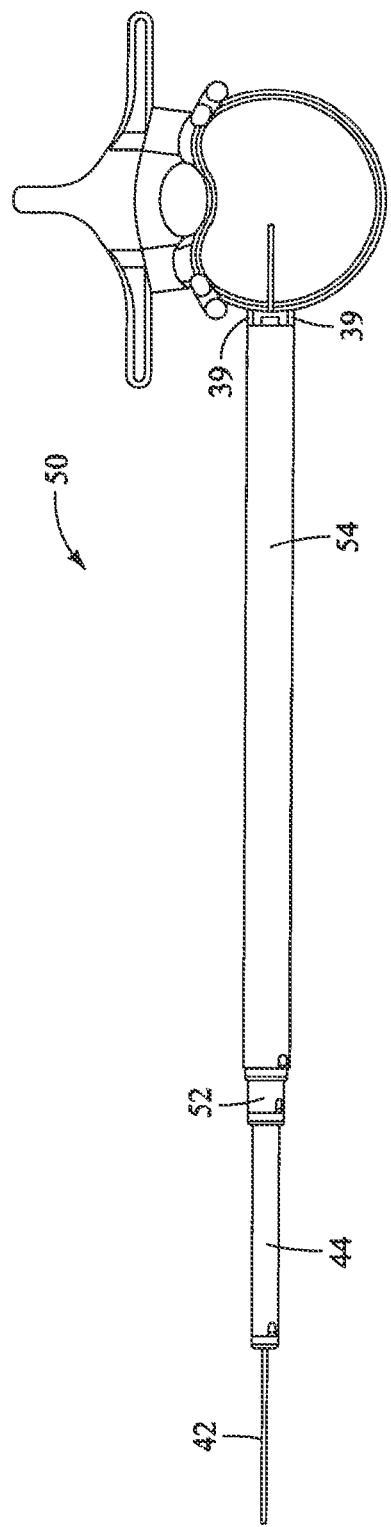
FIG. 12 is a side view illustrating the use of a secondary distraction assembly (comprising a plurality of dilating cannulae over the K-wire) to further distract tissue between the skin of the patient and the surgical target site according to the present invention.

Following this initial distraction, a secondary distraction may be optionally undertaken, such as via a sequential dilation system 50 as shown in FIG. 12. According to the present invention, the sequential dilation system 50 may include the K-wire 42, the initial dilator 44, and one or more supplemental dilators 52, 54 for the purpose of further dilating the tissue down to the surgical target site. Once again, each component of the secondary distraction assembly 50 (namely, the K-wire 42, the initial dilator 44, and the supplemental dilators 52, 54 may be, according to the present invention, provided with one or more electrodes (preferably at their distal regions) equipped for use with a nerve surveillance system, such as, by way of example, the type shown and described in the NeuroVision PCT Applications.

Figure 13:
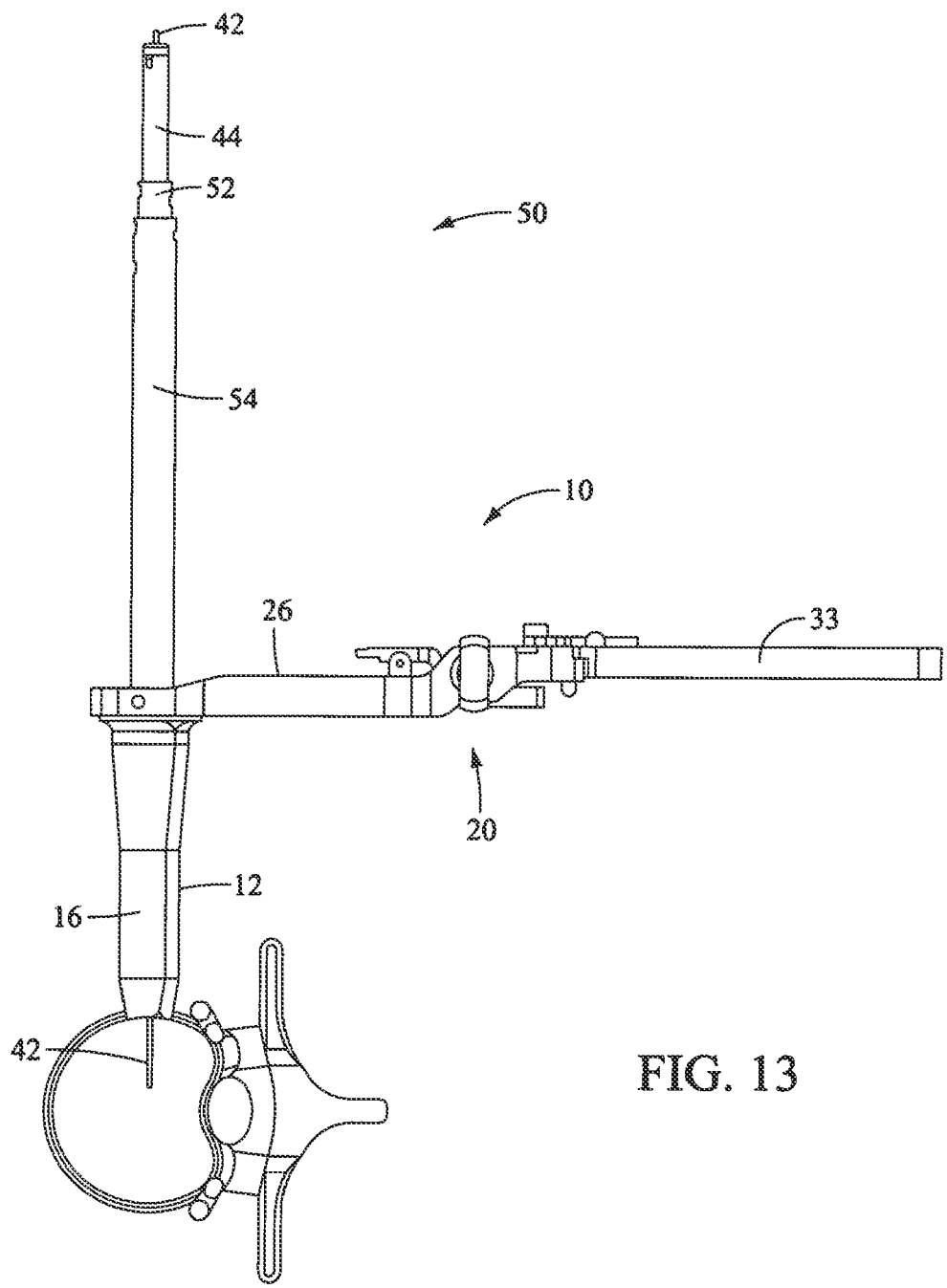
FIG. 13 is a side view of a retractor assembly according to the present invention, comprising a handle assembly having three (3) retractor blades extending there from (posterior, cephalad-most, and caudal-most) disposed over the secondary distraction assembly of FIG. 12 (shown in a first, closed position)
Figure 14:
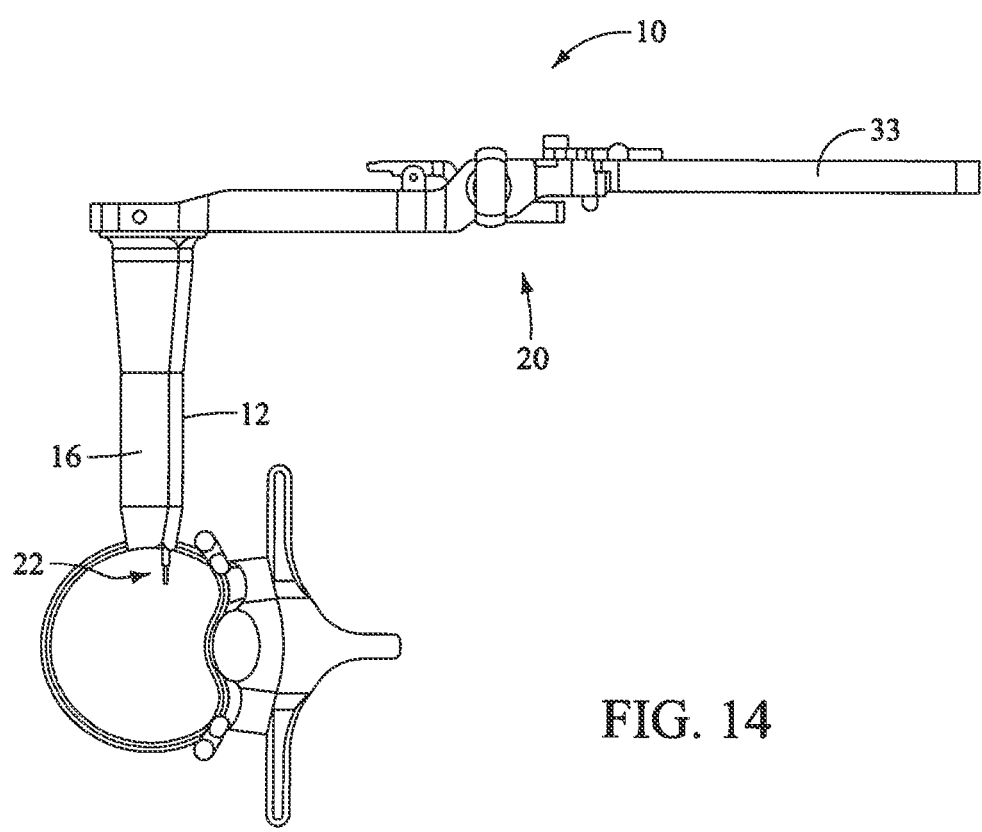
FIG. 14 is a side view of a retractor assembly according to the present invention, comprising a handle assembly having three (3) retractor blades extending there from (posterior, cephalad-most, and caudal-most) with the secondary distraction assembly of FIG. 12 removed and shim element introduced.
Figure 15:
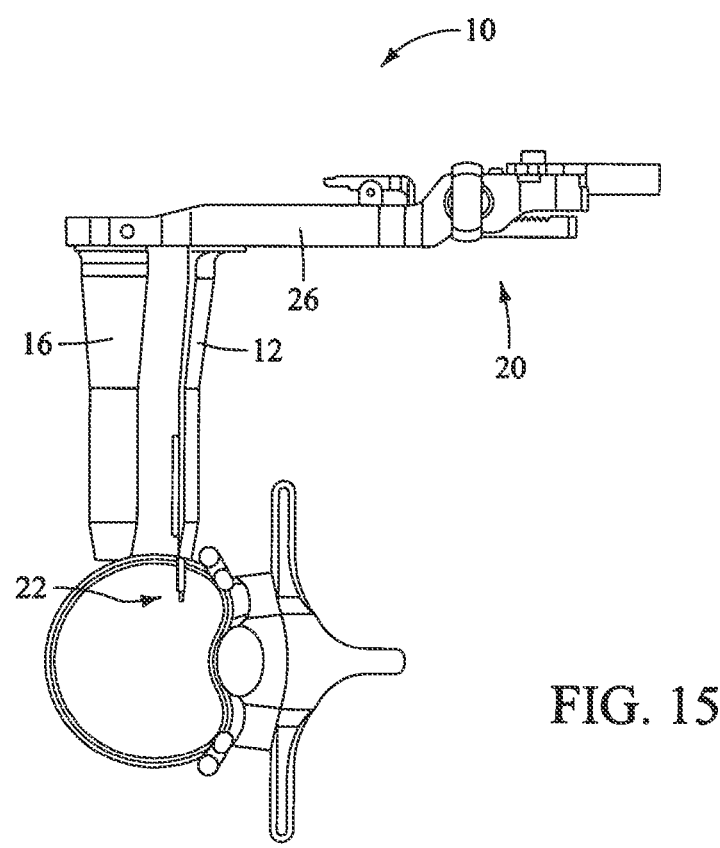
FIGS. 15-16 are perspective and top views, respectively, of the retractor assembly in a second, opened (i.e. retracted) position to thereby create an operative corridor to a surgical target site according to the present invention.
Figure 16:
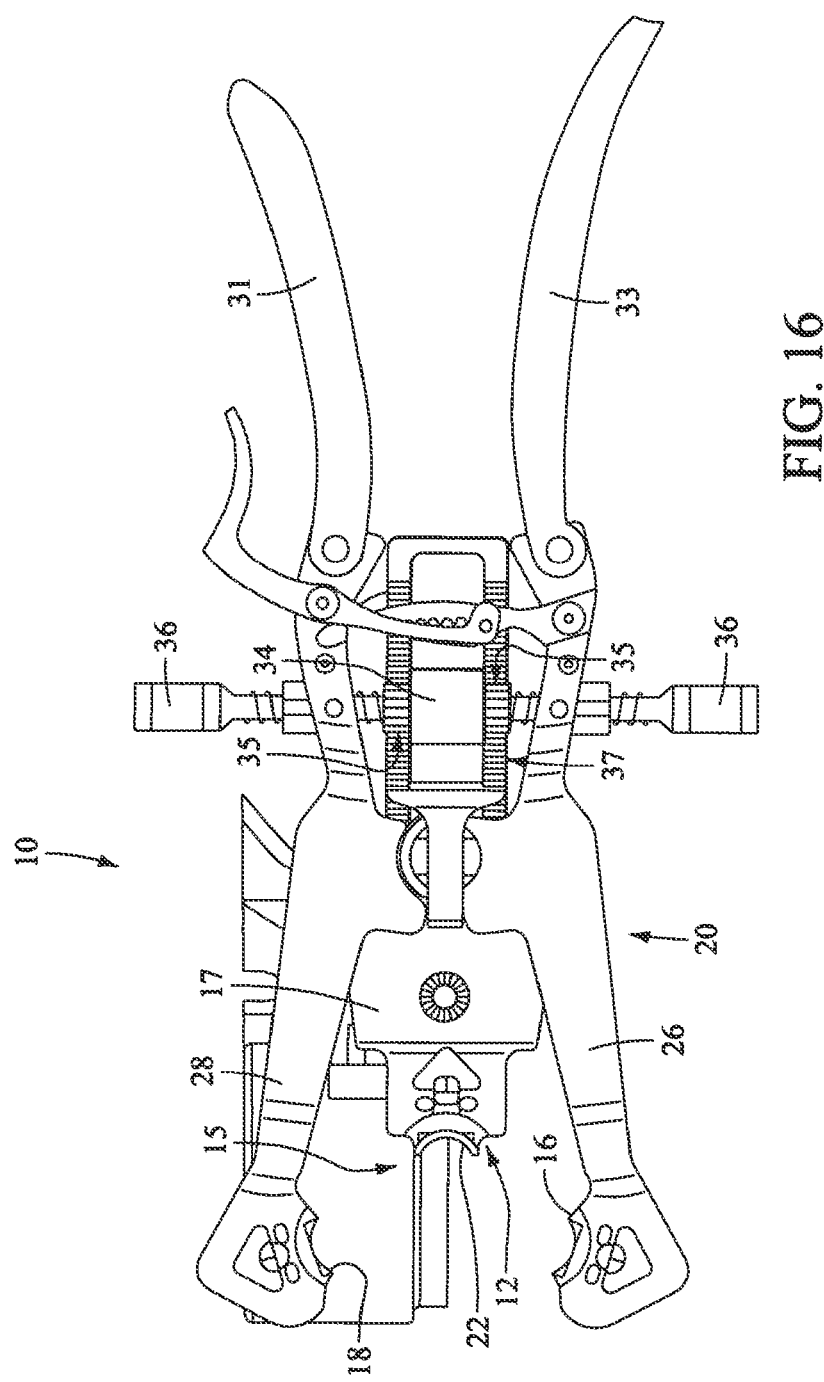
Figure 17:
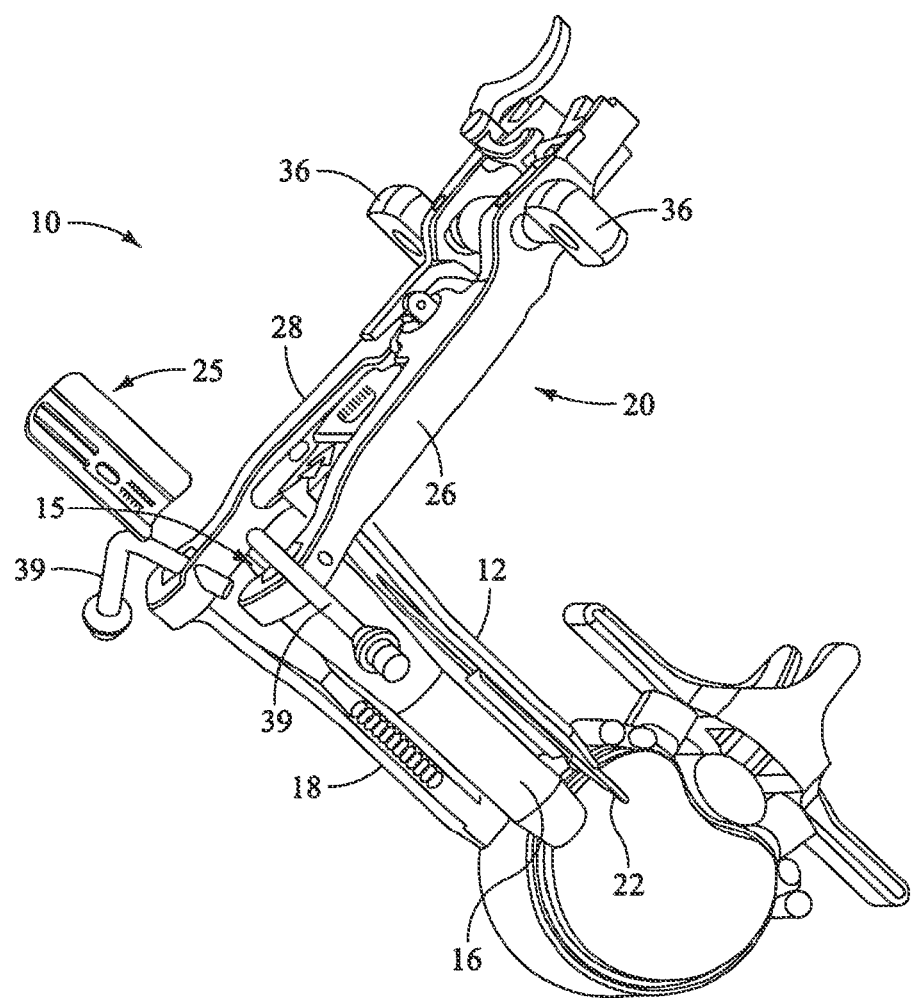
FIGS. 17-18 are perspective and side views, respectively, of the retractor assembly in the second, opened (i.e. retracted) position (with the secondary distraction assembly removed) and with the retractor extenders of FIGS. 4-5 and 6-7 coupled to the retractor according to the present invention.
Figure 18:
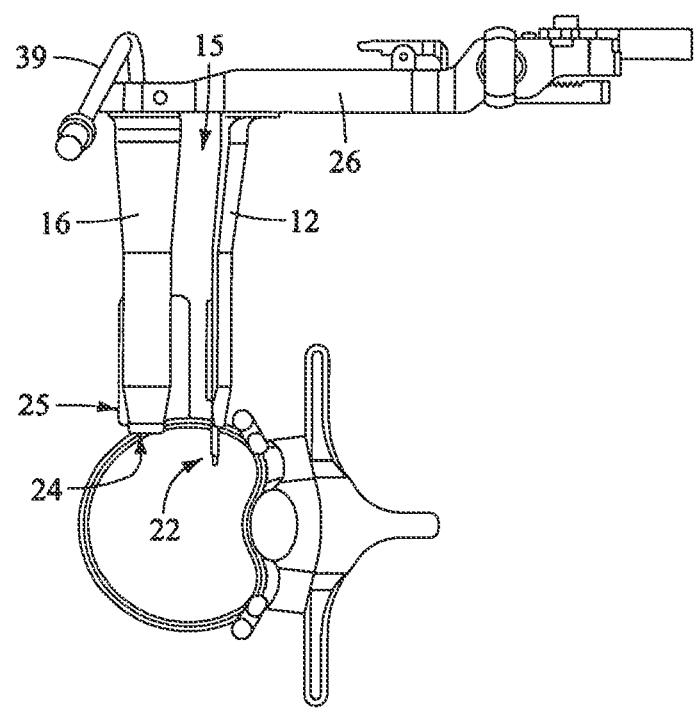

As shown in FIG. 13, the retraction assembly 10 of the present invention is thereafter advanced along the exterior of the sequential dilation system 50. This is accomplished by maintaining the retractor blades 12, 16, 18 in a first, closed position (with the retractor blades 12-16 in generally abutting relation to one another). Once advanced to the surgical target site, the sequential dilation assembly 50 may be removed and the shim element 22 engaged with the posterior refractor blade 12 such that the distal end thereof extends into the disc space as shown in FIG. 14. At this point, the handle assembly 20 may be operated to move the retractor blades 16, 18 into a second, open or "retracted" position as shown generally in FIGS. 15-16. As one can see, the posterior retractor blade 12 is allowed to stay in the same general position during this process, such that the cephalad-most and caudal-most refractor blades 14, 16 move away from the posterior retractor blade 12. At this point, the narrow and wide retractor extenders 24, 25 may be engaged with the caudal-most retractor blade 18 and cephalad-most retractor blade 16, respectively, as shown in FIGS. 17-18.

As mentioned above, any number of distraction components and/or retraction components (including but not limited to those described herein) may be equipped to detect the presence of (and optionally the distance and/or direction to) neural structures during the steps tissue distraction and/or retraction. This is accomplished by employing the following steps: (1) one or more stimulation electrodes are provided on the various distraction and/or retraction components; (2) a stimulation source (e.g. voltage or current) is coupled to the stimulation electrodes; (3) a stimulation signal is emitted from the stimulation electrodes as the various components are advanced towards or maintained at or near the surgical target site; and (4) the patient is monitored to determine if the stimulation signal causes muscles associated with nerves or neural structures within the tissue to innervate. If the nerves innervate, this may indicate that neural structures may be in close proximity to the distraction and/or retraction components.

Neural monitoring may be accomplished via any number of suitable fashions, including but not limited to observing visual twitches in muscle groups associated with the neural structures likely to found in the tissue, as well as any number of monitoring systems, including but not limited to any commercially available "traditional" electromyography (EMG) system (that is, typically operated by a neurophysiologist). Such monitoring may also be carried out via the surgeon-driven EMG monitoring system shown and described in the following commonly owned and co-pending NeuroVision PCT Applications referenced above. In any case (visual monitoring, traditional EMG and/or surgeon-driven EMG monitoring), the access system of the present invention may advantageously be used to traverse tissue that would ordinarily be deemed unsafe or undesirable, thereby broadening the number of manners in which a given surgical target site may be accessed.

Figure 19:
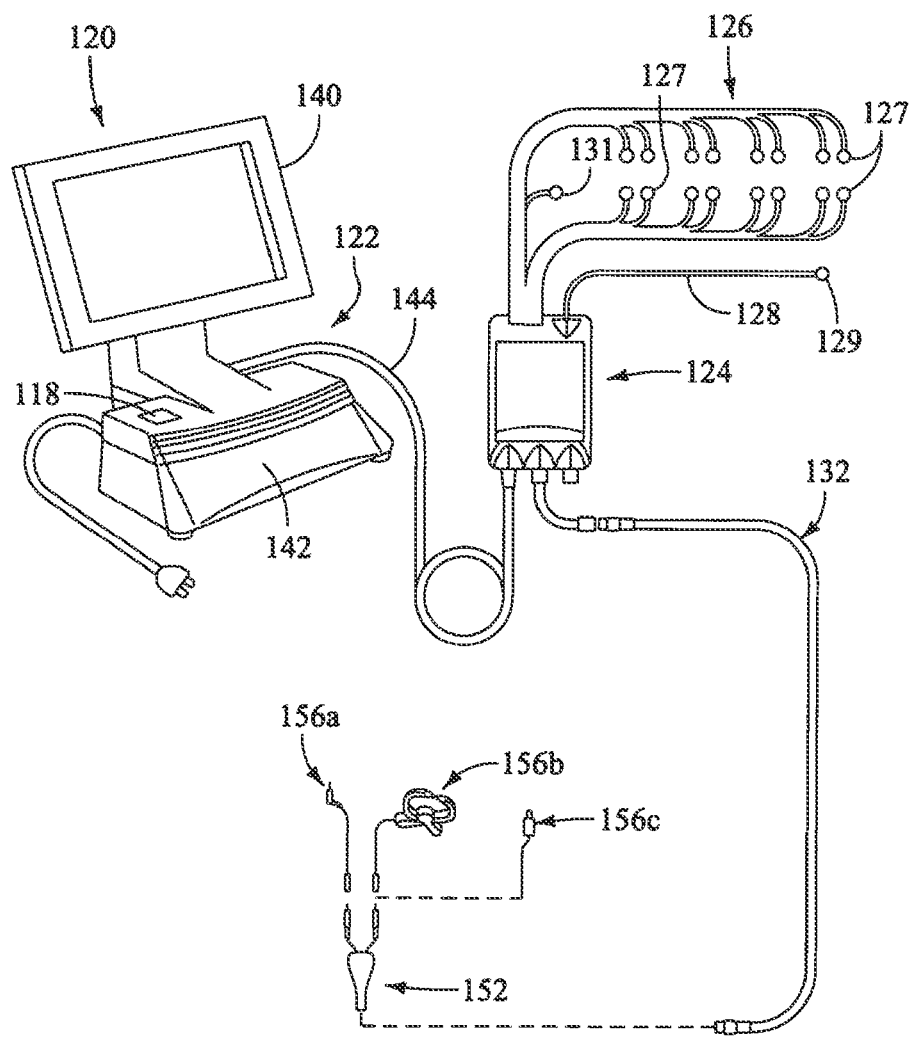
FIG. 19 is a perspective view of an exemplary nerve monitoring system capable of performing nerve monitoring before, during and after the creating of an operative corridor to a surgical target site using the surgical access system in accordance with the present invention.
Figure 20:
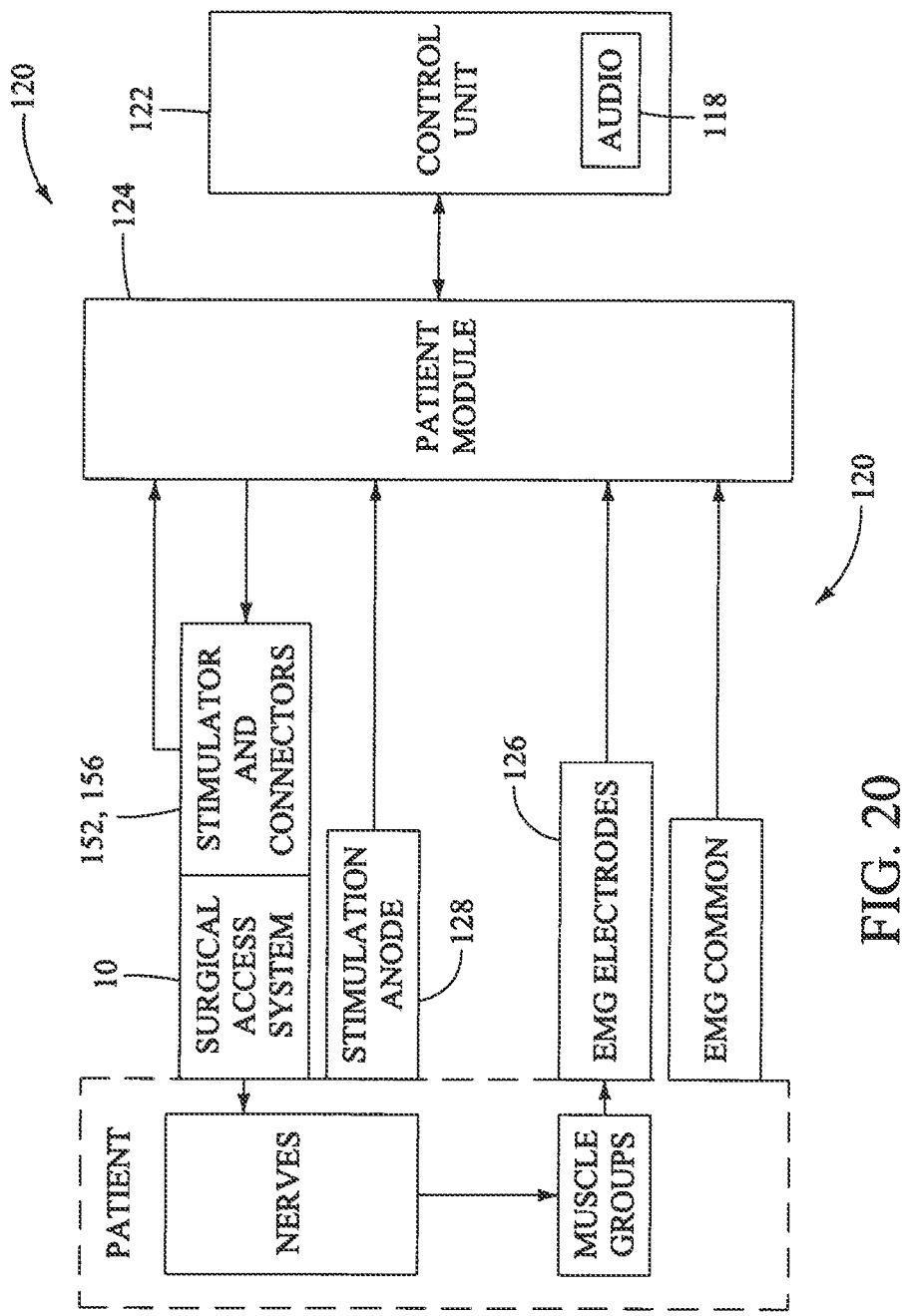
FIG. 20 is a block diagram of the nerve monitoring system shown in FIG. 19.

FIGS. 19-20 illustrate, by way of example only, a monitoring system 120 of the type disclosed in the NeuroVision PCT Applications suitable for use with the surgical access system 10 of the present invention. The monitoring system 120 includes a control unit 122, a patient module 124, and an EMG harness 126 and return electrode 128 coupled to the patient module 124, and a cable 132 for establishing electrical communication between the patient module 124 and the surgical access system of the present invention (retractor assembly 10 of FIG. 1 and distraction assemblies 40, 50 of FIGS. 9-12). More specifically, this electrical communication can be achieved by providing, by way of example only, a hand-held stimulation controller 152 capable of selectively providing a stimulation signal (due to the operation of manually operated buttons on the hand-held stimulation controller 152) to one or more connectors 156a, 156b, 156c. The connectors 156a, 156b, 156c are suitable to establish electrical communication between the hand-held stimulation controller 152 and (by way of example only) the stimulation electrodes on the K-wire 42, the dilators 44, 48, 52, 54, the refractor blades 12, 16, 18 and/or the shim members 22, 24, 25 (collectively "surgical access instruments").

In order to use the monitoring system 120, then, these surgical access instruments must be connected to the connectors 156a, 156b and/or 156c, at which point the user may selectively initiate a stimulation signal (preferably, a current signal) from the control unit 122 to a particular surgical access instruments. Stimulating the electrode(s) on these surgical access instruments before, during and/or after establishing operative corridor will cause nerves that come into close or relative proximity to the surgical access instruments to depolarize, producing a response in a myotome associated with the innervated nerve.

The control unit 122 includes a touch screen display 140 and a base 142, which collectively contain the essential processing capabilities (software and/or hardware) for controlling the monitoring system 120. The control unit 122 may include an audio unit 118 that emits sounds according to a location of a surgical element with respect to a nerve. The patient module 124 is connected to the control unit 122 via a data cable 144, which establishes the electrical connections and communications (digital and/or analog) between the control unit 122 and patient module 124. The main functions of the control unit 122 include receiving user commands via the touch screen display 140, activating stimulation electrodes on the surgical access instruments, processing signal data according to defined algorithms, displaying received parameters and processed data, and monitoring system status and report fault conditions. The touch screen display 140 is preferably equipped with a graphical user interface (GUI) capable of communicating information to the user and receiving instructions from the user. The display 140 and/or base 142 may contain patient module interface circuitry (hardware and/or software) that commands the stimulation sources, receives digitized signals and other information from the patient module 124, processes the EMG responses to extract characteristic information for each muscle group, and displays the processed data to the operator via the display 140.

In one embodiment, the monitoring system 120 is capable of determining nerve direction relative to one or more of the K-wire 42, the dilators 44, 48, 52, 54, the retractor blades 12, 16, 18 and/or the shim elements 22, 24, 25 before, during and/or following the creation of an operative corridor to a surgical target site. Monitoring system 120 accomplishes this by having the control unit 122 and patient module 124 cooperate to send electrical stimulation signals to one or more of the stimulation electrodes provided on these instruments. Depending upon the location of the surgical access system 10 within a patient (and more particularly, to any neural structures), the stimulation signals may cause nerves adjacent to or in the general proximity of the surgical access system 10 to depolarize. This causes muscle groups to innervate and generate EMG responses, which can be sensed via the EMG harness 126. The nerve direction feature of the system 120 is based on assessing the evoked response of the various muscle myotomes monitored by the system 120 via the EMG harness 126.

By monitoring the myotomes associated with the nerves (via the EMG harness 126 and recording electrode 127) and assessing the resulting EMG responses (via the control unit 122), the surgical access system 10 is capable of detecting the presence of (and optionally the distant and/or direction to) such nerves. This provides the ability to actively negotiate around or past such nerves to safely and reproducibly form the operative corridor to a particular surgical target site, as well as monitor to ensure that no neural structures migrate into contact with the surgical access system 10 after the operative corridor has been established. In spinal surgery, for example, this is particularly advantageous in that the surgical access system 10 may be particularly suited for establishing an operative corridor to an intervertebral target site in a postero-lateral, trans-psoas fashion so as to avoid the bony posterior elements of the spinal column.

Figure 21:
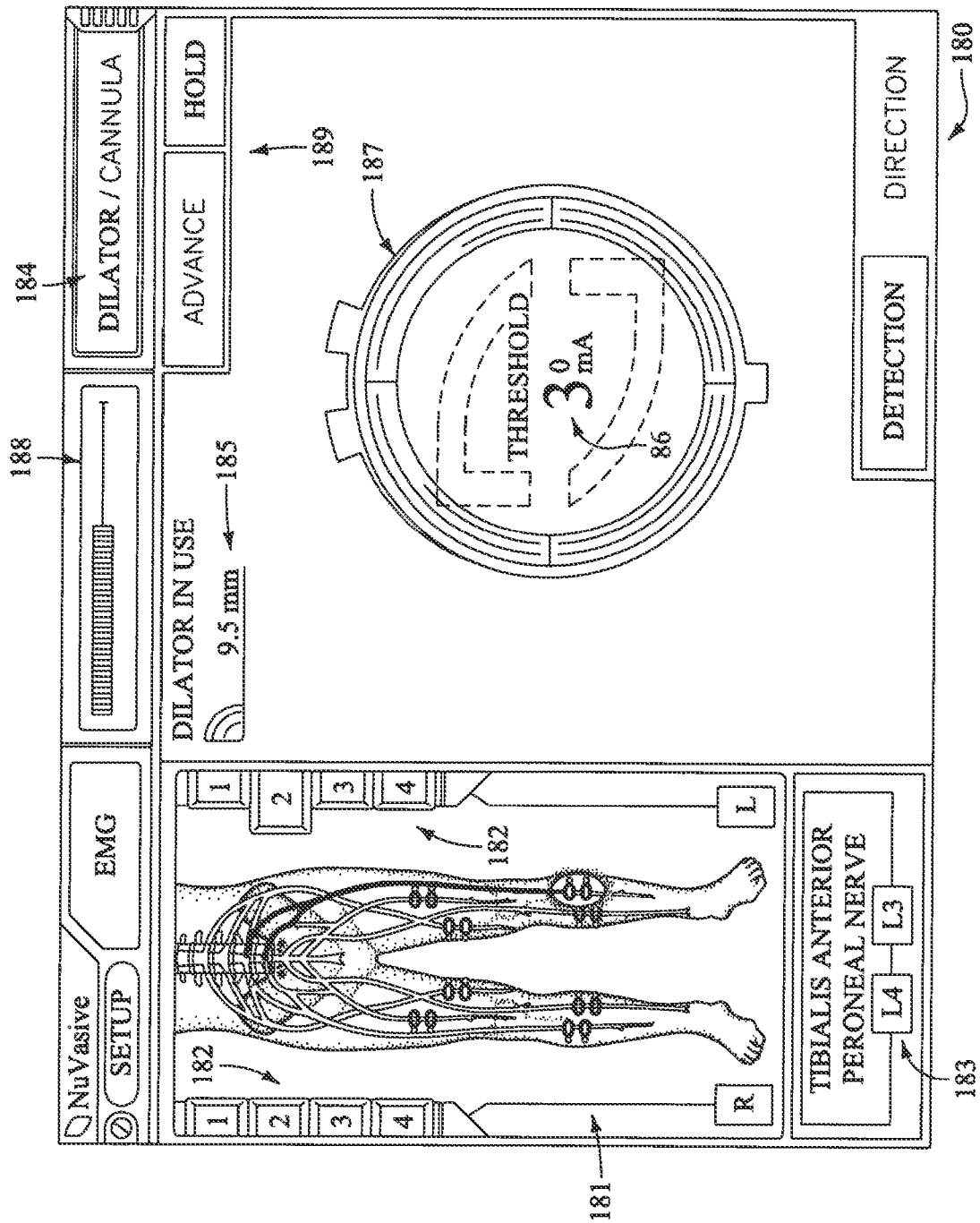
FIGS. 21-22 are screen displays illustrating exemplary features and information communicated to a user during the use of the nerve monitoring system of FIG. 19.
Figure 22:
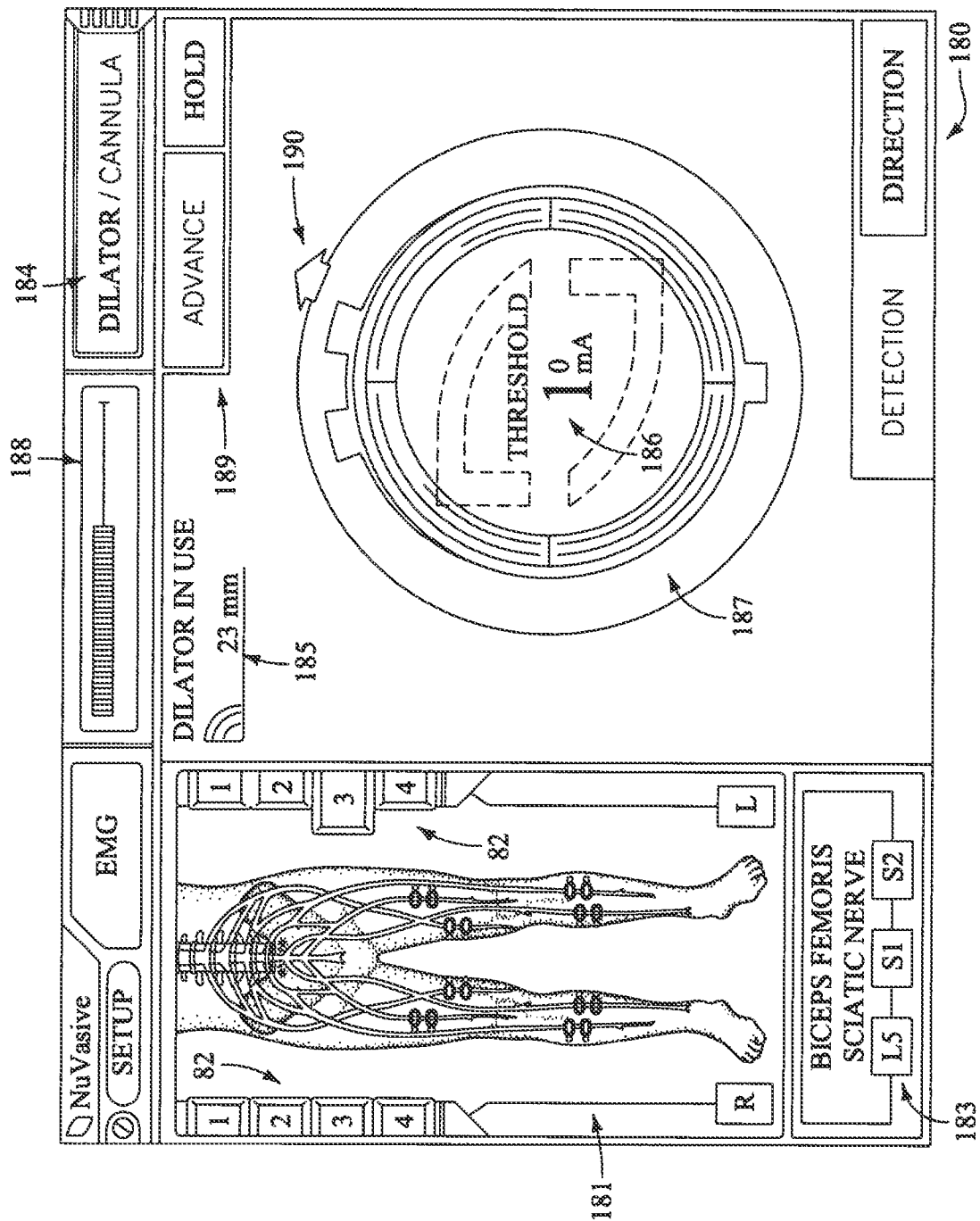

FIGS. 21-22 are exemplary screen displays (to be shown on the display 140) illustrating one embodiment of the nerve direction feature of the monitoring system shown and described with reference to FIGS. 19-20. These screen displays are intended to communicate a variety of information to the surgeon in an easy-to-interpret fashion. This information may include, but is not necessarily limited to, a display of the function 180 (in this case "DIRECTION"), a graphical representation of a patient 181, the myotome levels being monitored 182, the nerve or group associated with a displayed myotome 183, the name of the instrument being used 184 (in this case, a dilator 46, 48), the size of the instrument being used 185, the stimulation threshold current 186, a graphical representation of the instrument being used 187 (in this case, a cross-sectional view of a dilator 44, 48) to provide a reference point from which to illustrate relative direction of the instrument to the nerve, the stimulation current being applied to the stimulation electrodes 188, instructions for the user 189 (in this case, "ADVANCE" and/or "HOLD"), and (in FIG. 22) an arrow 190 indicating the direction from the instrument to a nerve. This information may be communicated in any number of suitable fashions, including but not limited to the use of visual indicia (such as alpha-numeric characters, light-emitting elements, and/or graphics) and audio communications (such as a speaker element). Although shown with specific reference to a dilating cannula (such as at 184), it is to be readily appreciated that the present invention is deemed to include providing similar information on the display 140 during the use of any or all of the various instruments forming the surgical access system 10 of the present invention, including the initial distraction assembly 40 (i.e. the K-wire 42 and dilators 44, 48) and/or the retractor blades 12, 16, 18 and/or the shim elements 22, 24, 25.

As evident from the above discussion and drawings, the present invention accomplishes the goal of gaining access a surgical target site in a fashion less invasive than traditional "open" surgeries and, moreover, does so in a manner that provides the ability to access such a surgical target site regardless of the neural structures required to be passed through (or near) in order to establish an operative corridor to the surgical target site. The present invention furthermore provides the ability to perform neural monitoring in the tissue or regions adjacent the surgical target site during any procedures performed after the operative corridor has been established. The surgical access system of the present invention can be used in any of a wide variety of surgical or medical applications, above and beyond the spinal applications discussed herein. Such spinal applications may include any procedure wherein instruments, devices, implants and/or compounds are to be introduced into or adjacent the surgical target site, including but not limited to discectomy, fusion (including PLIF, ALIF, TLIF and any fusion effectuated via a lateral or far-lateral approach and involving, by way of example, the introduction of bone products (such as allograft or autograft) and/or devices having ceramic, metal and/or plastic construction (such as mesh) and/or compounds such as bone morphogenic protein), total disc replacement, etc. . . .).

Moreover, the surgical access system of the present invention opens the possibility of accessing an increased number of surgical target sites in a "less invasive" fashion by eliminating or greatly reducing the threat of contacting nerves or neural structures while establishing an operative corridor through or near tissues containing such nerves or neural structures. In so doing, the surgical access system of the present invention represents a significant advancement capable of improving patient care (via reduced pain due to "less-invasive" access and reduced or eliminated risk of neural contact before, during, and after the establishment of the operative corridor) and lowering health care costs (via reduced hospitalization based on "less-invasive" access and increased number of suitable surgical target sites based on neural monitoring). Collectively, these translate into major improvements to the overall standard of care available to the patient population, both domestically and overseas.

What is claimed is:

1. A system for accessing a surgical target site, comprising:
   a retractor assembly having a plurality of blades releasably coupled to a handle assembly, said plurality of blades capable of being advanced simultaneously to said surgical target site while in a closed position and thereafter selectively opened to create a customized operative corridor to said surgical target site;
   a stimulation electrode coupled to the retractor assembly;
   a patient module;
   a cable electrically coupling the stimulation electrode with the patient module;
   a sensor harness coupled to the patient module; and
   a control unit in communication with the patient module and having a touch screen display, wherein the system is configured to:
      send electrical stimulation signals via the stimulation electrode;
      sense a response to the electrical stimulation with the sensor harness;
      assess the response to the electrical stimulation; and
      provide, at the touch screen display, a user interface based on the assessed response.

2. The system of claim 1, wherein the control unit is configured to:
   receive a user command over the touch screen display; and
   cause activation of the stimulation electrode based on the user command.

3. The system of claim 1, wherein the patient module is configured to digitize the response to the electrical stimulation and send data regarding the digitized response to the control unit.

4. The system of claim 1, wherein the system is configured to determine nerve direction relative to the plurality of blades.

5. The system of claim 4, wherein to determine the nerve direction includes to:
   assess evoked responses of one or more muscle myotomes.

6. The system of claim 1, wherein to provide the user interface includes to provide a user interface that includes at least one of the following:
   a graphical representation of a patient;
   myotome levels being monitored;
   a name of an instrument being used;
   a size of the instrument being used;
   a graphical representation of the instrument being used;
   a stimulation current being applied;
   an instruction to a user; and
   an indication of a direction from the instrument to a nerve.

7. The system of claim 1, wherein to provide the user interface includes to provide a user interface that includes at least two of the following:
   a graphical representation of a patient;
   myotome levels being monitored;
   a name of an instrument being used;
   a size of the instrument being used;
   a graphical representation of the instrument being used;
   a stimulation current being applied;
   an instruction to a user; and
   an indication of a direction from the instrument to a nerve.

8. The system of claim 1, wherein to provide the user interface includes to provide a user interface that includes at least three of the following:
   a graphical representation of a patient;
   myotome levels being monitored;
   a name of an instrument being used;
   a size of the instrument being used;
   a graphical representation of the instrument being used;
   a stimulation current being applied;
   an instruction to a user; and
   an indication of a direction from the instrument to a nerve.

9. The system of claim 1, wherein the retractor assembly includes:
   ratchet-like grooves; and
   one or more teeth configured to engaged within the ratchet-like grooves in response to manual actuation by a user.

* * * * *